United States Patent
Kanamori

(10) Patent No.: US 10,307,057 B2
(45) Date of Patent: Jun. 4, 2019

(54) EYE IMAGING APPARATUS

(71) Applicant: Panasonic Intellectual Property Management Co., Ltd., Osaka (JP)

(72) Inventor: Katsuhiro Kanamori, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/885,910

(22) Filed: Feb. 1, 2018

(65) Prior Publication Data

US 2018/0220887 A1    Aug. 9, 2018

(30) Foreign Application Priority Data

Feb. 7, 2017    (JP) .................................. 2017-020341

(51) Int. Cl.
*A61B 3/14*    (2006.01)
*A61B 3/12*    (2006.01)
(Continued)

(52) U.S. Cl.
CPC .............. *A61B 3/14* (2013.01); *A61B 3/117* (2013.01); *A61B 3/12* (2013.01); *G02B 27/144* (2013.01); *G02B 27/14* (2013.01); *G02B 27/286* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| 6,104,431 A | 8/2000 | Inoue et al. | |
| 2009/0149742 A1* | 6/2009 | Kato | A61B 5/117 600/425 |

(Continued)

FOREIGN PATENT DOCUMENTS

| EP | 2415393 | 2/2012 |
| JP | 11-101935 | 4/1999 |

(Continued)

OTHER PUBLICATIONS

Yasufumi Fukuma et al., "Polarization Analysis of Fundus Using Polarization Measurement Camera", Japanese journal of visual science, 28(3), Sep. 2007, pp. 110-116 (Partial Translation).

(Continued)

*Primary Examiner* — Mohammed A Hasan
(74) *Attorney, Agent, or Firm* — Wenderoth, Lind & Ponack, L.L.P.

(57) ABSTRACT

An eye imaging apparatus includes a lighting device including a fundus illuminator and a cornea illuminator; a half mirror; an imaging device including a camera having a first objective lens; and a first polarizer. The first polarizer is disposed between the half mirror and the camera. The fundus illuminator irradiates the half mirror with first light polarized in a direction orthogonal to a transmission axis of the first polarizer. The half mirror receives the first light and outputs resulting light to an eye. A travel direction of the resulting light is in alignment with an optical axis of the first objective lens. The cornea illuminator emits light at a timing different from an emission timing of the first light, and the eye is irradiated with second light based on the light emitted by the cornea illuminator from a direction different from a direction parallel with the optical axis.

16 Claims, 32 Drawing Sheets

(51) Int. Cl.
*A61B 3/117* (2006.01)
*G02B 27/14* (2006.01)
*G02B 27/28* (2006.01)

(58) Field of Classification Search
USPC .......................................................... 351/206
See application file for complete search history.

(56) References Cited

U.S. PATENT DOCUMENTS

2012/0249957 A1    10/2012  Shibata et al.
2013/0010262 A1*    1/2013  Sato ..................... A61B 3/102
                                                                  351/206
2014/0347628 A1    11/2014  Martinez Corral et al.
2014/0347631 A1    11/2014  Kishida et al.

FOREIGN PATENT DOCUMENTS

JP    2014-530697    11/2014
JP    2016-122912     7/2016
JP    2016-122913     7/2016
WO    2010/044791     4/2010

OTHER PUBLICATIONS

Kazuo Ishikawa et al., "Application of polarization property to clinical medicine in the occular imaging system", Journal of Ophthalmological Optics Society of Japan, vol. 10, No. 1, Mar. 1989, pp. 93-96 (Partial Translation).
Kuniyuki Kugenuma et al., "Disparity estimation and image synthesis from low-SNR multi-aperture images", Optics & Photonics Japan 2016, 31aES9, Oct. 2016 (Whole Sentence Translation).

* cited by examiner

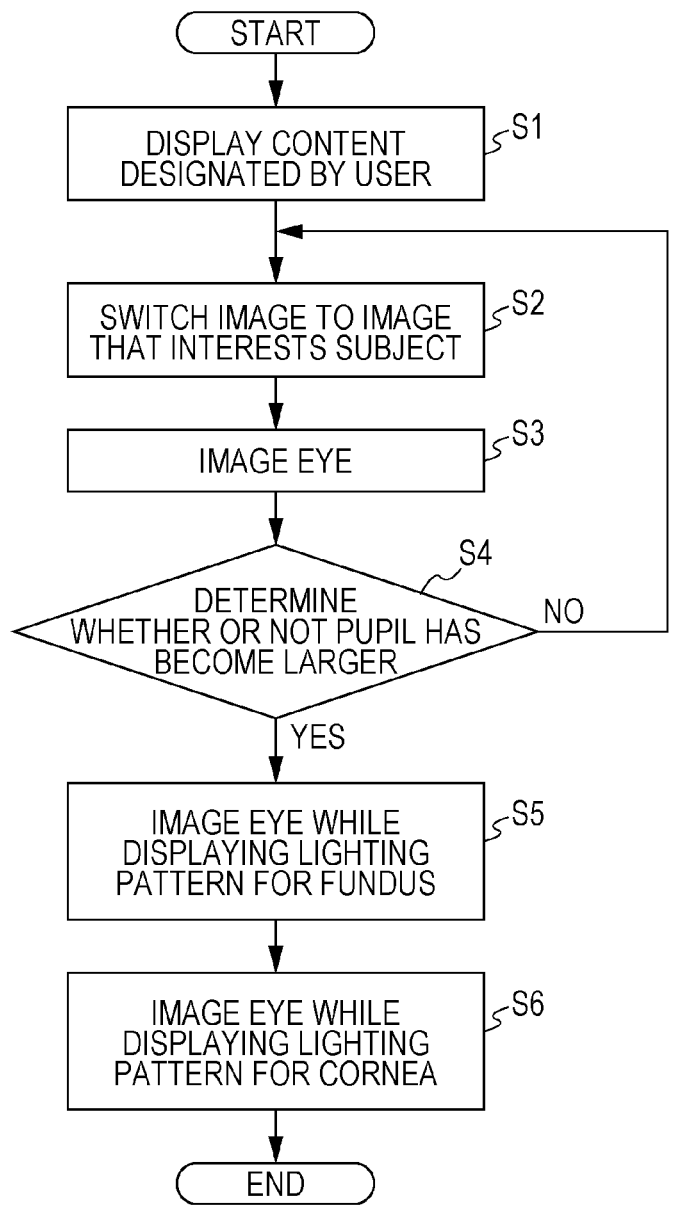

EYE IMAGING APPARATUS

BACKGROUND

1. Technical Field

The present disclosure relates to an eye imaging apparatus.

2. Description of the Related Art

Polarization is used for inspection of products and parts (see, for example, Japanese Unexamined Patent Application Publication No. 2016-122913 and Japanese Unexamined Patent Application Publication No. 2016-122912). Furthermore, studies on application of polarization to imaging of an eye have been conducted (see, for example, Yasufumi FUKUMA et al. "Polarization Analysis of Fundus Using Polarization Measurement Camera", Japanese Journal of Visual Science, Sep. 26, 2007, Vol. 28, No. 3, pp. 110-116 (hereinafter referred to as Non-Patent Literature 1) and Kazuo ISHIKAWA et al. "Application of polarization property to clinical medicine in the ocular imaging system", Journal of Ophthalmological Optics Society of Japan, March 1989, pp. 93-96 (hereinafter referred to as Non-Patent Literature 2)). For example, a change of intraocular pressure can appear as deformation of a cornea. It is known that blood glucose concentration in aqueous humor of a patient with diabetes is higher than a normal person, and there is a report that Alzheimer's disease can be diagnosed by observing a retinal nerve of a fundus. That is, observation of an eye leads to detection of not only eye diseases but also other diseases, and therefore there are demands to obtain more information by imaging an eye.

SUMMARY

However, conventional inspection using a fundus camera, a slit lamp, optical coherence tomography (OCT), and the like requires imaging portions of an eye by using different devices at a position close to the eye while fixing a face of a subject. Therefore, it takes time to complete inspection, and the subject feels great stress. Development of a technique for more easily obtaining an image concerning a fundus of an eye and an image concerning a cornea in a non-contact manner without need to fix the eye is beneficial.

One non-limiting and exemplary embodiment of the present disclosure provides the following.

In one general aspect, the techniques disclosed here feature an eye imaging apparatus including: a lighting device; a half mirror; an imaging device; and a first polarizer. The lighting device includes a fundus illuminator and a cornea illuminator. The imaging device includes a first camera having a first objective lens. The first polarizer is disposed between the half mirror and the first camera. The fundus illuminator irradiates the half mirror with first light polarized in a direction orthogonal to a transmission axis of the first polarizer. The half mirror receives the first light and outputs resulting light to an eye, a travel direction of the resulting light being in alignment with an optical axis of the first objective lens. The cornea illuminator emits light at a timing different from a timing at which the fundus illuminator emits the first light. Second light based on the light emitted by the cornea illuminator irradiates the eye from a direction different from a direction parallel with the optical axis of the first objective lens.

It should be noted that general or specific embodiments may be implemented as an element, a device, a module, a system, an integrated circuit, a method, and a computer program. Alternatively, general or specific embodiments may be implemented as any selective combination of an apparatus, an element, a device, a module, a system, an integrated circuit, a method, and a computer program.

According to the present disclosure, it is possible to provide an eye imaging apparatus that can more easily obtain an image concerning a fundus of an eye and an image concerning a cornea of the eye.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 14 is a view schematically illustrating an example of an image of an eye obtained in a state where a plurality of light sources of light emitting units are on;

FIG. 15 is a view schematically illustrating an example of an image of an eye obtained in a state where a plurality of light sources of light emitting units are on;

FIG. 25 is a flowchart for explaining an example of an eye imaging operation performed by an eye imaging apparatus;

DETAILED DESCRIPTION

Figure 1:
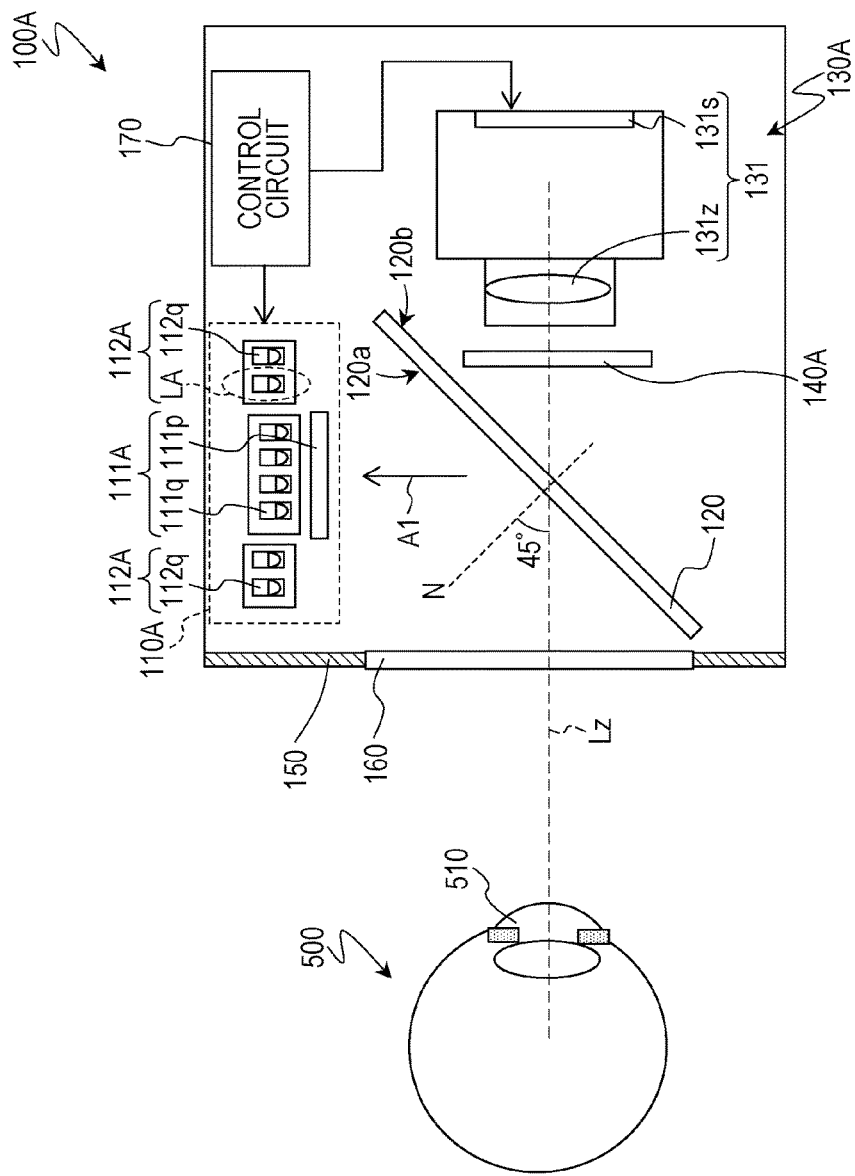
FIG. 1 is a view schematically illustrating an exemplary configuration of an eye imaging apparatus according to First Embodiment of the present disclosure.

An aspect of the present disclosure is outlined as follows.

[Item 1]

An eye imaging apparatus includes:

a lighting device;

a half mirror;

an imaging device; and a first polarizer.

The lighting device includes a fundus illuminator and a cornea illuminator.

The imaging device includes a first camera having a first objective lens.

The first polarizer is disposed between the half mirror and the first camera.

The fundus illuminator irradiates the half mirror with first light polarized in a direction orthogonal to a transmission axis of the first polarizer.

The half mirror receives the first light and outputs resulting light to an eye, a travel direction of the resulting light being in alignment with an optical axis of the first objective lens.

The cornea illuminator emits light at a timing different from a timing at which the fundus illuminator emits the first light.

Second light based on the light emitted by the cornea illuminator irradiates the eye from a direction different from a direction parallel with the optical axis of the first objective lens.

[Item 2]

In the eye imaging apparatus according to Item 1, the cornea illuminator is disposed to surround the fundus illuminator and includes a plurality of light emitters that emit the light, the half mirror is irradiated with the light that is unpolarized light, and the second light is light reflected by the half mirror.

[Item 3]

In the eye imaging apparatus according to Item 1, the cornea illuminator is disposed to surround the first objective lens when viewed along the optical axis and includes a plurality of light emitters that emit the light, the half mirror is irradiated with the light that is unpolarized light, and the second light is light that has passed through the half mirror.

[Item 4]

In the eye imaging apparatus according to Item 1, the cornea illuminator includes a plurality of light emitters that emit the light, the cornea illuminator is disposed on a side of the half mirror opposite to a side on which the first camera is disposed, and the plurality of light emitters are disposed not to overlap the optical axis and not to overlap a straight line that is parallel with the optical axis and that intersects with the first objective lens.

[Item 5]

In the eye imaging apparatus according to any one of Items 2 through 4, the plurality of light emitters include a plurality of first light sources and a plurality of second light sources, the cornea illuminator includes first linearly polarizing plates disposed in front of the respective first light sources, transmission axes of the respective first linearly polarizing plates are orthogonal to the transmission axis of the first polarizer, and the plurality of first light sources emit light at a timing different from a timing at which the plurality of second light sources emit light.

[Item 6]

In the eye imaging apparatus according to any one of Items 1 through 5, the imaging device further includes a second camera having a second objective lens, and the first polarizer is disposed between the half mirror and the second camera.

[Item 7]

In the eye imaging apparatus according to Item 6, a focal length of the second objective lens is shorter than a focal length of the first objective lens.

[Item 8]

In the eye imaging apparatus according to Item 6, the imaging device includes a plurality of first cameras, the plurality of first cameras include the first cameras, the plurality of first cameras include a plurality of first objective lenses, the plurality of first objective lenses include the first objective lenses, the plurality of first cameras correspond to the respective plurality of first objective lenses, and the plurality of first objective lenses surround the second objective lens when viewed along the optical axis.

[Item 9]

In the eye imaging apparatus according to Item 8, a focal length of the second objective lens is shorter than a focal length of each of the plurality of first objective lenses.

[Item 10]

In the eye imaging apparatus according to Item 1, the lighting device is a display having a display surface, the fundus illuminator includes a first region of the display surface and a second polarizer disposed in front of the first region, a transmission axis of the second polarizer is orthogonal to the transmission axis of the first polarizer, and the cornea illuminator includes a second region of the display surface, the second region surrounding the first region.

[Item 11]

The eye imaging apparatus according to Item 10, further includes a control circuit that drives the lighting device and the imaging device in synchronization with each other.

The display switches a displayed image among a plurality of images.

The control circuit causes the imaging device to detect mydriasis of the eye, and upon detection of mydriasis, the control circuit causes the fundus illuminator to emit the first light and causes the imaging device to image the eye.

[Item 12]

In the eye imaging apparatus according to Item 11, following the imaging under the first light, the control circuit causes the fundus illuminator to finish the irradiation with the first light, and causes the imaging device to image the eye while causing the cornea illuminator to emit light.

[Item 13]

In the eye imaging apparatus according to Item 1, one of the fundus illuminator and the cornea illuminator includes a first light emitter including a first linearly polarizing plate, a second light emitter including a second linearly polarizing plate, a third light emitter including a third linearly polarizing plate, and a fourth light emitter including a first circularly polarizing plate, directions of transmission axes of the first, second, and third linearly polarizing plates are different from one another, and one of the transmission axes of the first, second, and third linearly polarizing plates is parallel with a polarization direction of the first light, the imaging device includes a plurality of first cameras each including the first camera, the first polarizer includes a fourth linearly polarizing plate having a transmission axis parallel with the polarization direction of the first light, a fifth linearly polarizing plate having a transmission axis orthogonal to the polarization direction of the first light, a sixth linearly polarizing plate having a transmission axis in a direction different from both of the transmission axis of the fourth linearly polarizing plate and the transmission axis of the fifth linearly polarizing plate, and a second circularly polarizing plate, and each of the fourth linearly polarizing plate, the fifth linearly polarizing plate, the sixth linearly polarizing plate, and the second circularly polarizing plate is disposed in front of one of the plurality of first cameras.

[Item 14]

In the eye imaging apparatus according to Item 13, the other one of the fundus illuminator and the cornea illuminator includes a fifth light emitter including a seventh linearly polarizing plate, a sixth light emitter including an eighth linearly polarizing plate, a seventh light emitter including a ninth linearly polarizing plate, and an eighth light emitter including a third circularly polarizing plate, and directions of transmission axes of the seventh, eighth, and ninth linearly polarizing plates are different from one another, and one of the transmission axes of the seventh, eighth, and ninth linearly polarizing plates is parallel with the polarization direction of the first light.

[Item 15]

In the eye imaging apparatus according to any one of Items 1 through 14, the imaging device is a light field camera.

[Item 16]

In the eye imaging apparatus according to any one of Items 1 through 15, the imaging device images a fundus of the eye while the eye is being irradiated with the reflected first light and images a cornea of the eye while the eye is being irradiated with the second light.

Embodiments of the present disclosure are described below with reference to the drawings. Each of the embodiments described below is a general or specific example.

Numerical values, shapes, materials, constituent elements, the way in which the constituent elements are disposed and connected, steps, the order of steps, and the like are examples and do not limit the present disclosure. Various aspects described herein can be combined as long as no inconsistency arises. Among constituent elements in the embodiment below, constituent elements that are not described in independent claims indicating highest concepts are described as optional constituent elements. Hereinafter, constituent elements having substantially the same functions are given identical reference signs, and description thereof is sometimes omitted.

First Embodiment

FIG. 1 schematically illustrates an exemplary configuration of an eye imaging apparatus according to First Embodiment of the present disclosure. An eye imaging apparatus 100A illustrated in FIG. 1 includes a lighting device 110A, a half mirror 120, an imaging device 130A, and a polarizer 140A. In the configuration illustrated in FIG. 1, the imaging device 130A includes a camera unit 131 including an image sensor 131s and an objective lens 131z disposed in front of the image sensor 131s. The half mirror 120 has a first surface 120a and a second surface 120b opposite to the first surface 120a and is disposed in the eye imaging apparatus 100A so that a normal N to the first surface 120a is inclined by approximately 45 degrees with respect to an optical axis Lz of the objective lens 131z, as illustrated in FIG. 1. The polarizer 140A is located between the second surface 120b of the half mirror 120 and the imaging device 130A.

The lighting device 110A includes a first illuminating unit 111A and a second illuminating unit 112A. The lighting device 110A typically includes a plurality of light sources. In this example, the first illuminating unit 111A includes a plurality of light sources 111q and a polarizer 111p disposed in front of the plurality of light sources 111q. As described later in detail, the first illuminating unit 111A offers light for imaging a fundus of an eye that is a subject. Each of the plurality of light sources 111q may be, for example, a known light-emitting element such as a white light emitting diode or an infrared light emitting diode. The polarizer 111p may be, for example, a commercially available polarizing sheet or a metal wire grid polarizer.

Meanwhile, the second illuminating unit 112A offers light for imaging a cornea of an eye. The second illuminating unit 112A includes a plurality of light emitting units LA. In this example, the second illuminating unit 112A includes a plurality of light sources 112q as in the first illuminating unit 111A, and each of the plurality of light sources 112q functions as a light emitting unit LA. Each of the plurality of light sources 112q may be a known light-emitting element such as a white light emitting diode or an infrared light emitting diode, as in the case of the plurality of light sources 111q. An optical axis of each of the plurality of light sources 111q and the plurality of light sources 112q forms an angle of 45 degrees with the normal N. In the configuration illustrated in FIG. 1, no polarizer is disposed in front of the plurality of light sources 112q.

The eye imaging apparatus 100A further includes a control circuit 170. The control circuit 170 controls operations of the lighting device 110A and the imaging device 130A so that the lighting device 110A and the imaging device 130A operate in synchronization with each other. For example, the control circuit 170 causes the image sensor 131s to obtain data of a first image of an eye 500 that is a subject by driving the image sensor 131s of the camera unit 131 in a state where the plurality of light sources 111q of the first illuminating unit 111A are selectively turned on, i.e., in a state where the plurality of light sources 111q are on and the plurality of light sources 112q are off. Furthermore, the control circuit 170 causes the image sensor 131s to obtain data of a second image of the eye 500 by driving the image sensor 131s of the camera unit 131 in a state where the plurality of light sources 111q of the first illuminating unit 111A are off and the plurality of light sources 112q of the second illuminating unit 112A are on. Such functions of the control circuit 170 may be realized by a combination of a general-purpose processing circuit and software or may be realized by hardware specialized for such processing.

A housing of the eye imaging apparatus 100A has, for example, a light shielding part 150 and a light transmitting part 160 supported by the light shielding part 150. The light transmitting part 160 is a transparent window made of a material such as glass or a transparent resin and has a function of preventing the half mirror 120 from becoming dirty. During imaging, position and posture of the eye imaging apparatus 100A are adjusted so that the eye 500 that is a subject is located on the optical axis Lz of the objective lens 131z. In this state, the light transmitting part 160 faces the eye 500. The eye 500 is an eye of a human or an animal.

The imaging device 130A is disposed on the second surface 120b side of the half mirror 120, whereas the lighting device 110A is disposed on the first surface 120a side of the half mirror 120 in the example illustrated in FIG. 1. That is, a configuration in which the first surface 120a of the half mirror 120 is irradiated with light emitted from the light sources of the lighting device 110A is illustrated in this example. The first surface 120a of the half mirror 120 is irradiated with light emitted from the lighting device 110A, and the eye 500 is irradiated with light reflected by the first surface 120a through the light transmitting part 160.

Figure 2:
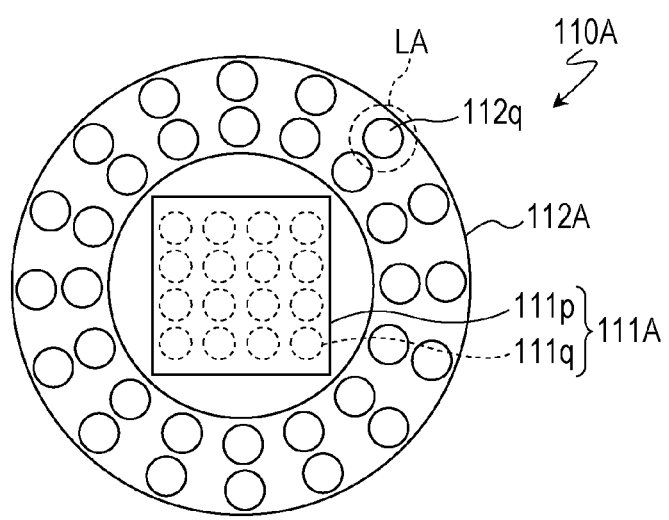
FIG. 2 is a view for explaining an exemplary configuration of a lighting device and is a plan view of the lighting device viewed from a direction indicated by arrow A1 in FIG. 1.

FIG. 2 illustrates an exemplary configuration of the lighting device 110A. FIG. 2 illustrates the lighting device 110A viewed from a direction indicated by arrow A1 in FIG. 1. In the configuration illustrated in FIG. 2, the first illuminating unit 111A is located close to a center of the lighting device 110A, and the plurality of light sources 111q of the first illuminating unit 111A are disposed in a matrix of four rows and four columns. The plurality of light sources 111q can be disposed on an identical surface. The shape of the first illuminating unit 111A is not limited to the rectangular shape illustrated in FIG. 2 and can be any shape. The polarizer 111p is disposed so as to cover the plurality of light sources 111q.

The first illuminating unit 111A of the lighting device 110A is disposed so that the optical axis of the first illuminating unit 111A passes close to an intersection of the half mirror 120 and the optical axis Lz. Since an optical axis of each of the plurality of light sources 111q forms an angle of 45 degrees with the normal N as described above, the eye 500 can be irradiated with polarized light in a state close to coaxial lighting in a case where the first illuminating unit 111A is disposed in this way. It may be assumed that the optical axis of the first illuminating unit 111A is an optical axis of a light source 111q located at a center or close to the center of the first illuminating unit 111A among the plurality of light sources 111q.

Meanwhile, the plurality of light emitting units LA, i.e., the plurality of light sources 112q of the second illuminating unit 112A are disposed in a ring shape so as to surround the first illuminating unit 111A in this example. By disposing the plurality of light emitting units LA, i.e., the plurality of light sources 112q of the second illuminating unit 112A around the first illuminating unit 111A, a cornea 510 (see FIG. 1) of the eye 500 can be uniformly irradiated, for example, with unpolarized light from directions different from light for imaging a fundus.

An exemplary operation of the eye imaging apparatus 100A is described below with reference to FIGS. 3 through 6. As is clear from the description below, according to the embodiment of the present disclosure, an image concerning a fundus of an eye of a subject (e.g., a human) and an image concerning a cornea surface of the eye of the subject can be obtained, for example, successively without restraining a face of the subject and without changing a physical configuration of a device for imaging an eye.

Figure 3:
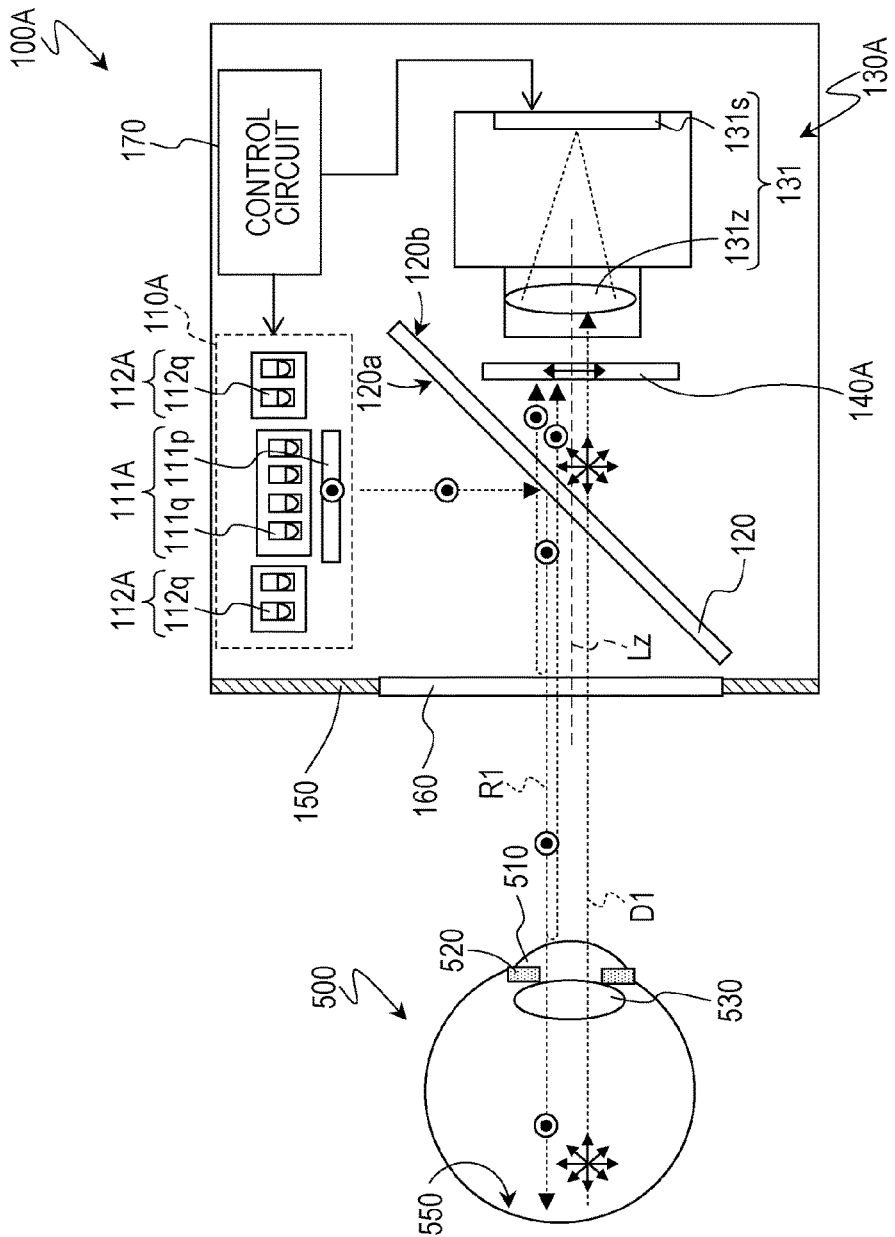
FIG. 3 is a view for explaining an operation during imaging of a fundus of an eye.

FIG. 3 is a view for explaining an operation during imaging of an image concerning a fundus of the eye 500. An imaging mode described below is sometimes referred to as a fundus imaging mode.

To obtain an image concerning a fundus, the control circuit 170 drives the lighting device 110A so that the plurality of light sources 111$q$ of the first illuminating unit 111A are on and the plurality of light sources 112$q$ of the second illuminating unit 112A are off among the plurality of light sources included in the lighting device 110A. Since the polarizer 111$p$ is disposed in front of the plurality of light sources 111$q$, a component that has an electric field vector oscillating in a direction that is aligned with a transmission axis of the polarizer 111$p$ among components of light emitted from the plurality of light sources 111$q$ passes through the polarizer 111$p$ and is then incident on the first surface 120$a$ of the half mirror 120. In other words, linearly-polarized light is incident on the first surface 120$a$ of the half mirror 120. The double circles in FIG. 3 indicate that an electric field vector oscillates in a direction perpendicular to the paper on which FIG. 3 is drawn.

The half mirror 120 reflects linearly-polarized light emitted from the first illuminating unit 111A. As described above, the normal N to the half mirror 120 forms an angle of 45 degrees with the optical axis of each of the plurality of light sources 111$q$ and the optical axis Lz of the objective lens 131$z$. Accordingly, as schematically illustrated in FIG. 3, a travel direction of the reflected light beam is almost in alignment with the optical axis Lz of the objective lens 131$z$. Note that the travel direction of the reflected light beam may have an error of approximately 3 degrees with respect to the optical axis Lz of the objective lens 131$z$. A polarization plane of the linearly-polarized light does not change when the linearly-polarized light is reflected by the half mirror 120. Accordingly, light R1 (hereinafter referred to simply as "reflected light R1") emitted from the first illuminating unit 111A and reflected by the half mirror 120 travels toward the eye 500 that is a subject while maintaining a polarization direction.

Part of the reflected light beam passes through the light transmitting part 160 and the cornea 510 of the eye 500 and then reaches an iris 520. Since the travel direction of the reflected light beam is almost in alignment with the optical axis Lz of the objective lens 131$z$, the light beam reflected by the half mirror 120 enters the eye 500 from directly above the eye 500, in other words, so that an incident angle is almost 0 degree on the basis of a line connecting the center of the eye 500 and the objective lens 131$z$. A large part of light that has passed through the cornea 510 passes through a pupil at a center of the iris 520 and a crystalline lens 530 and then reaches the fundus 550.

Light that has reached the fundus 550 is diffusely-reflected by the fundus 550 and travels from the eye 500 toward the eye imaging apparatus 100A as unpolarized return light D1. The return light D1 passes the crystalline lens 530, the pupil at the center of the iris 520, and the cornea 510, passes through the half mirror 120 from the first surface 120$a$ side to the second surface 120$b$ side, and then reaches the polarizer 140A. It may be considered that a reason why the unpolarized return light D1 is generated is that linearly-polarized light is cancelled because of occurrence of multiple scattering and absorption of light in layers such as an optic nerve layer and a blood vessel layer of the fundus.

In FIG. 3, the thick double-headed arrow in the rectangle representing the polarizer 140A indicates a direction of a transmission axis of the polarizer 140A. In this example, the transmission axis of the polarizer 140A is parallel with a top-bottom direction of the paper on which FIG. 3 is drawn. The expression "a direction of a transmission axis" as used herein refers to a direction in which the transmission axis extends when viewed from a direction facing a main surface of the polarizer. The return light D1 generated by diffuse reflection by the fundus 550 of the eye 500 is unpolarized light as described above, and at least part of the return light D1, for example, an almost half in terms of intensity passes through the polarizer 140A.

The control circuit 170 causes the image sensor 131$s$ to execute imaging in synchronization with lighting of the plurality of light sources of the first illuminating unit 111A. The imaging device 130A is controlled on the basis of an instruction from the control circuit 170, and thereby an image of a fundus based on the light that has passed through the polarizer 140A can be obtained by the camera unit 131.

Light travelling toward the imaging device 130A contains a component specular-reflected, for example, by the light transmitting part 160 and the cornea 510 among components of the light R1 reflected by the half mirror 120, as schematically illustrated in FIG. 3. These reflected light beams generated by specular reflection generate bright spots in an image of a fundus and are therefore unnecessary for observation of the fundus.

In this example, the transmission axis of the polarizer 111$p$ of the first illuminating unit 111A is perpendicular to the paper on which FIG. 3 is drawn, and the transmission axis of the polarizer 140A disposed in front of the camera unit 131 is parallel with the top-bottom direction of the paper on which FIG. 3 is drawn. That is, a configuration in which the transmission axis of the polarizer 111$p$ and the transmission axis of the polarizer 140A are orthogonal to each other is employed in this example. The first illuminating unit 111A irradiates the half mirror 120 with light polarized in a direction orthogonal to the transmission axis of the polarizer 140A, and specular reflection at the light transmitting part 160, the cornea 510, and the like does not change a polarization plane of the incident linearly-polarized light. Accordingly, an oscillation direction of an electric field vector of light specular-reflected by the light transmitting part 160, the cornea 510, and the like is the same as an oscillation direction of an electric field vector of the reflected light R1. That is, the oscillation direction of the electric field vector of light specular-reflected by the light transmitting part 160, the cornea 510, and the like is orthogonal to the transmission axis of the polarizer 140A, and therefore the light specular-reflected by the light transmitting part 160, the cornea 510, and the like is blocked by the polarizer 140A. This prevents an image (bright spot) of unnecessary reflected light from appearing in an image of a fundus. Since unnecessary light resulting from specular reflection is blocked by the polarizer 140A, an image of a fundus can be obtained, for example, even in a case where the eye imaging apparatus 100A is moved away by approximately a distance of distinct vision (10 cm to 20 cm).

Figure 4:
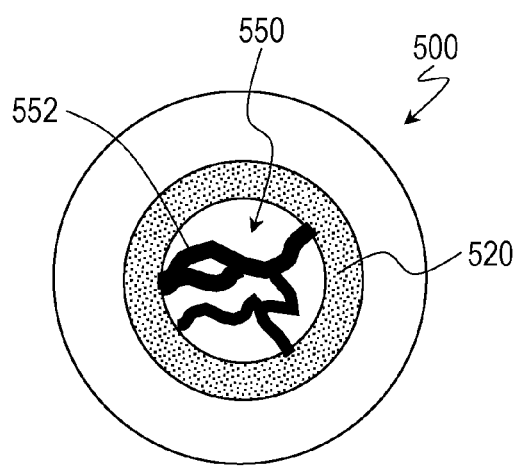
FIG. 4 is a view schematically illustrating an example of an image of an eye obtained in a fundus imaging mode.

FIG. 4 schematically illustrates an example of an image of an eye obtained in the fundus imaging mode. As described with reference to FIG. 3, the eye 500 can be irradiated with polarized light in a state close to coaxial lighting in the fundus imaging mode. Therefore, a bright image of the fundus 550 can be obtained as schematically illustrated in FIG. 4. Since multiple reflection in the eye 500 can be prevented, it is possible to prevent an image of light that is generated by multiple reflection in the eye 500 and hinders observation of a fundus from appearing in an obtained image. Furthermore, since entry of light specular-reflected by the cornea 510 into the camera unit 131 can be prevented by the polarizer 140A, appearance of an image of light that is generated by specular reflection at the cornea 510 and hinders observation of a fundus is also prevented. It is therefore possible to obtain an image clearly showing texture concerning, for example, a blood vessel 552 on retina.

Next, an operation during imaging of an image concerning the cornea 510 is described with reference to FIG. 5. An imaging mode described below is sometimes referred to as a cornea imaging mode.

Figure 5:
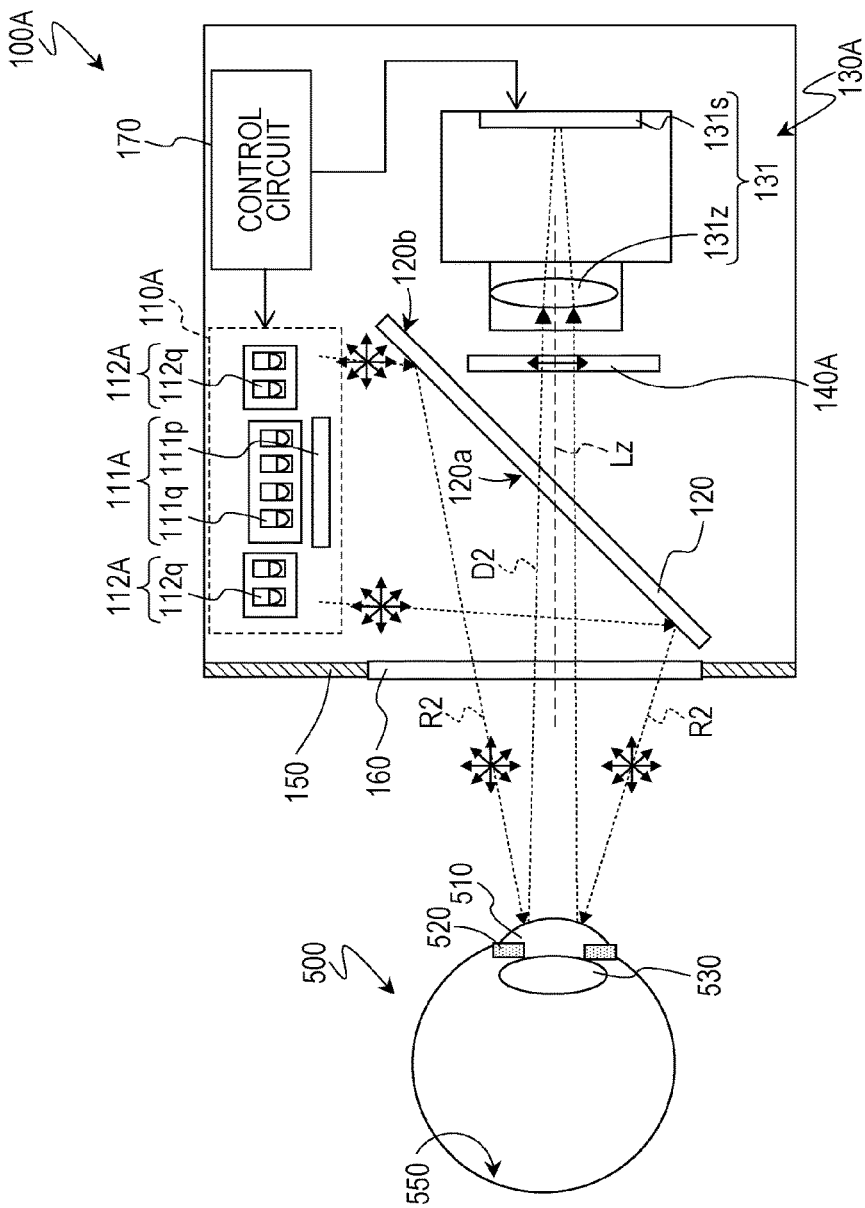
FIG. 5 is a view for explaining an operation during imaging of a cornea of the eye.

FIG. 5 is a view for explaining an operation during imaging of the cornea 510 of the eye 500. In the cornea imaging mode, the control circuit 170 causes the plurality of light sources 112q of the second illuminating unit 112A to turn on and causes the plurality of light sources 111q of the first illuminating unit 111A to turn off. Since no polarizer is disposed in front of the plurality of light sources 112q of the second illuminating unit 112A, the second illuminating unit 112A irradiates the first surface 120a of the half mirror 120 with unpolarized light as schematically illustrated in FIG. 5. The half mirror 120 reflects the unpolarized light emitted from the second illuminating unit 112A. Reflected light R2 that is light (unpolarized light in this case) emitted from the second illuminating unit 112A and then reflected by the half mirror 120 is directed toward the eye 500 by the half mirror 120. The reflected light R2 reflected by the half mirror 120 is unpolarized light.

As described with reference to FIG. 2, the plurality of light sources 112q of the second illuminating unit 112A are disposed so as to surround the first illuminating unit 111A. Therefore, the reflected light R2 (unpolarized light in this case) enters the eye 500 from directions different from a direction parallel with the optical axis Lz of the objective lens 131z, in other words, from an oblique direction, as schematically illustrated in FIG. 5. Furthermore, since the plurality of light sources 112q of the second illuminating unit 112A are disposed in a ring shape around the first illuminating unit 111A, the cornea 510 of the eye 500 can be uniformly irradiated with light emitted from the second illuminating unit 112A and then reflected by the half mirror 120.

When the reflected light R2 reaches the eye 500, the cornea 510 generates return light D2 due to specular reflection. The return light D2 passes through the half mirror 120 and travels toward the camera unit 131. Since the return light D2 is also unpolarized light, part of the return light D2 passes through the polarizer 140A and forms an image of the eye 500 on an imaging surface of the image sensor 131s.

Figure 6:
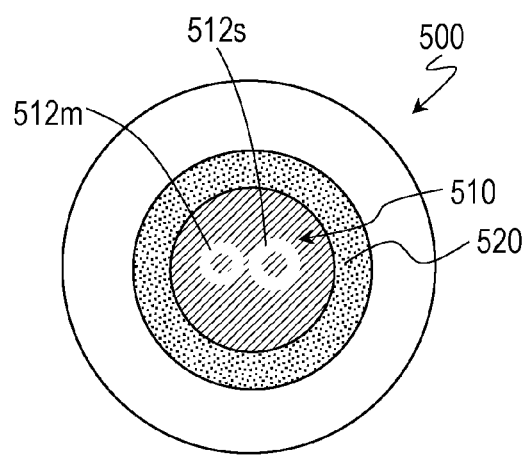
FIG. 6 is a view schematically illustrating an example of an image of an eye obtained in a cornea imaging mode.

FIG. 6 schematically illustrates an example of an image of an eye obtained in the cornea imaging mode. As schematically illustrated in FIG. 6, in the cornea imaging mode, a pupil appears as a dark part in an image in contrast with the fundus imaging mode.

In the cornea imaging mode, the second illuminating unit 112A irradiates the eye 500 from directions different from a direction parallel with the optical axis Lz of the objective lens 131z. Since the plurality of light sources 112q of the second illuminating unit 112A are disposed in a ring shape around the first illuminating unit 111A as described with reference to FIG. 2, light (unpolarized light in this case) emitted from the plurality of light sources 112q and reflected by the half mirror 120 enters the eye 500 at a larger incident angle with respect to a line connecting the center of the eye 500 and the objective lens 131z. Therefore, even if part of the reflected light R2 passes through the pupil, almost all of the light that has passed through the pupil is not directed toward the camera unit 131 because of multiple reflection in the eye 500. Accordingly, the pupil in the image obtained in the cornea imaging mode appears as a dark part. However, part of light that has passed through the pupil can enter the camera unit 131 as return light after multiple reflection in the eye 500. In the example illustrated in FIG. 6, a ring-shaped bright part 512m appears in the image in background of the dark pupil due to such return light. In this example, a ring-shaped bright part 512s also appears in the image due to specular reflection on the surface of the cornea 510 and vicinity thereof.

As described above, the imaging device 130A images the fundus 550 of the eye 500 while the eye 500 is being irradiated with the reflected light R1 of light emitted from the first illuminating unit 111A. Furthermore, the imaging device 130A images the cornea 510 of the eye 500 while the eye 500 is being irradiated with the reflected light R2 of light emitted from the second illuminating unit 112A. According to the above embodiment, the eye 500 can be irradiated with light (e.g., linearly-polarized light) travelling in a direction that is in alignment with the optical axis Lz of the objective lens 131z and light (e.g., unpolarized light) from directions different from a direction parallel with the optical axis Lz at respective different timings by a single device. For example, imaging (the fundus imaging mode) under illumination of polarized light that is close to coaxial lighting and imaging (the cornea imaging mode) under illumination of unpolarized light from a direction of a larger incident angle can be executed at respective different timings.

According to the embodiment of the present disclosure, imaging in the fundus imaging mode and imaging in the cornea imaging mode can be switched without changing a physical configuration of an optical system for lighting and an optical system for imaging. For example, data of an image concerning a fundus of an eye and data of an image concerning a cornea of the same eye can be sequentially obtained successively by switching these modes speedily (e.g., at intervals of approximately 30 milliseconds). Such an operation of the eye imaging apparatus according to the embodiment of the present disclosure can be achieved, for example, by a combination of a general-purpose processing circuit and software, and two types of images concerning an eye can be obtained speedily. It is therefore possible to image an eye without giving stress to a subject without need to restrain the face of the subject. The embodiment of the present disclosure is effective especially for imaging of an eye of a subject (e.g., an infant or an animal) who hardly obeys a doctor's instruction.

Imaging of a subject in the fundus imaging mode and imaging of the same subject in the cornea imaging mode can be executed in any order. For example, imaging in the fundus imaging mode may be executed after imaging in the cornea imaging mode. Furthermore, imaging in the fundus imaging mode and imaging in the cornea imaging mode can be exerted at any time intervals. However, in a case where imaging in these modes is sequentially executed at short time intervals by using visible light as first and second light, it is beneficial to execute imaging in the fundus imaging mode and imaging in the cornea imaging mode in this order after enlarging a pupil by darkening a room. This is because an image of a fundus can be obtained with more certainty.

In the fundus imaging mode, a half mirror is irradiated with polarized light having an electric field vector that oscillates in a direction orthogonal to a transmission axis of a polarizer disposed in front of a camera unit, and an eye is irradiated from almost directly above with light reflected by the half mirror, as described with reference to FIG. 3. Since lighting in the fundus imaging mode is lighting close to coaxial lighting, information concerning colors of a fundus can be obtained, for example, by using a color image sensor. Furthermore, since a transmission axis of a polarizer disposed in front of a camera unit and a polarization direction of linearly-polarized light with which a half mirror is irradiated are orthogonal to each other, influence of light generated by specular reflection (e.g., specular reflection at a cornea) that hinders observation of a fundus can be removed by the polarizer disposed in front of the camera unit. It is therefore possible to obtain a high-quality image concerning a fundus.

In the above example, the first illuminating unit 111A irradiates the half mirror 120 with S-polarized light, as schematically illustrated in FIG. 3. By irradiating the half mirror 120 with S-polarized light, higher reflectance can be obtained, and light use efficiency can be improved, as compared with the half mirror 120 is irradiated with P-polarized light. That is, a brighter image can be obtained.

Meanwhile, in the cornea imaging mode, an eye is irradiated, for example, with unpolarized light from an oblique direction at a timing different from a timing of irradiation with light for imaging a fundus. An image obtained on the basis of return light offers useful information for observation of a foreign substance, a scratch, and the like on a cornea surface.

As described above, according to the embodiment of the present disclosure, it is possible to obtain an image concerning a fundus and an image concerning a cornea more easily in a shorter period.

Modifications of First Embodiment

The eye imaging apparatus according to the embodiment of the present disclosure is not limited to the above example and can be modified in various ways. For example, the lighting device can be modified in various ways. Needless to say, configurations described below are merely examples, and a modification of the lighting device is not limited to the configurations described below.

Figure 7:
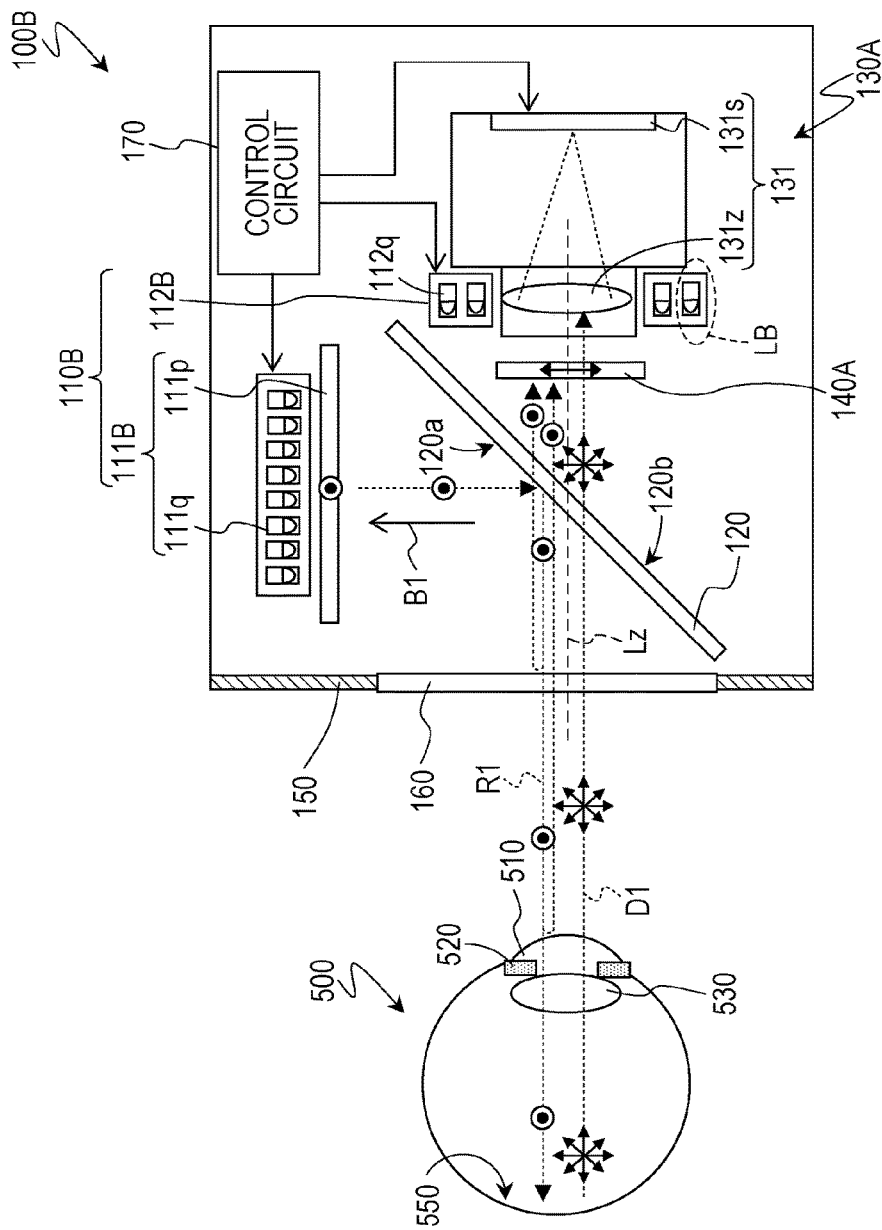
FIG. 7 is a view for explaining an exemplary configuration of an eye imaging apparatus according to a first modification of First Embodiment and an operation in the fundus imaging mode.

FIG. 7 illustrates a first modification of the eye imaging apparatus. An eye imaging apparatus 100B illustrated in FIG. 7 is different from the eye imaging apparatus 100A described with reference to FIG. 1 in that the eye imaging apparatus 100B includes a lighting device 110B instead of the lighting device 110A.

In the configuration illustrated in FIG. 7, the lighting device 110B includes a first illuminating unit 111B including a plurality of light sources 111q and a polarizer 111p and a second illuminating unit 112B including a plurality of light emitting units LB. As schematically illustrated in FIG. 7, the plurality of light emitting units LB are disposed on a second surface 120b of a half mirror so as to surround an objective lens 131z of a camera unit 131. As in the example described with reference to FIG. 2, the second illuminating unit 112B includes a plurality of light sources 112q as the light emitting units LB. In the configuration illustrated in FIG. 7, a polarizer 140A does not cover the plurality of light emitting units LB of the second illuminating unit 112B.

Figure 8:
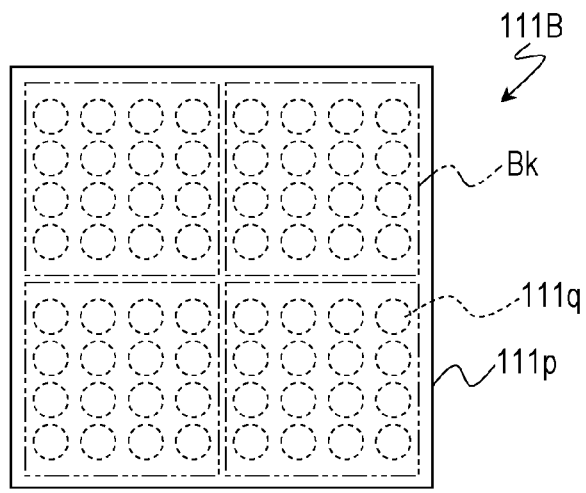
FIG. 8 is a view for explaining an exemplary configuration of a first illuminating unit of a lighting device and illustrates the first illuminating unit viewed from a direction indicated by arrow B1 in FIG. 7.

FIG. 8 illustrates the first illuminating unit 111B viewed from a direction indicated by arrow B1 in FIG. 7. In the configuration illustrated in FIG. 8, the first illuminating unit 111B includes four light emitting blocks Bk arranged in a matrix of two rows and two columns, and each of the light emitting blocks Bk includes light sources 111q arranged in four rows and four columns (sixteen light sources 111q in total), as in the first illuminating unit 111A of the eye imaging apparatus 100A. That is, the first illuminating unit 111B has four times as many light sources 111q as the first illuminating unit 111A of the eye imaging apparatus 100A. The polarizer 111p covers these plurality of light sources 111q.

As illustrated in FIG. 7, the second illuminating unit 112B is not disposed around the first illuminating unit 111B of the lighting device 110B unlike the first illuminating unit 111A of the eye imaging apparatus 100A. Therefore, more light sources 111q can be included in the first illuminating unit 111B by enlarging the first illuminating unit 111B. By thus disposing the first illuminating unit 111B and the second illuminating unit 112B separately in the eye imaging apparatus 100B, it is possible to increase the area of the first illuminating unit 111B, thereby illuminating the eye 500 (especially the fundus 550) more brightly.

FIG. 7 schematically illustrates an operation of the eye imaging apparatus 100B in the fundus imaging mode. The operation of the eye imaging apparatus 100B in the fundus imaging mode is similar to that of the eye imaging apparatus 100A. For example, the plurality of light sources 111q of the first illuminating unit 111B are turned on and the light sources 112q of the second illuminating unit 112B are turned off under control of a control circuit 170. Light emitted from the plurality of light sources 111q enters the polarizer 111p. A direction (a direction perpendicular to the paper on which FIG. 7 is drawn) orthogonal to a transmission axis of the polarizer 140A disposed in front of the camera unit 131 is selected as a direction of a transmission axis of the polarizer 111p. Accordingly, the first illuminating unit 111B irradiates the half mirror 120 with light polarized in a direction orthogonal to the transmission axis of the polarizer 140A. The half mirror 120 reflects the light toward the eye 500 as reflected light R1 travelling in a direction that is alignment with the optical axis Lz of the objective lens 131z. Part of return light D1 that enters the eye 500 and is diffusely reflected by the fundus 550 passes through the polarizer 140A and forms an image concerning the fundus 550.

Figure 9:
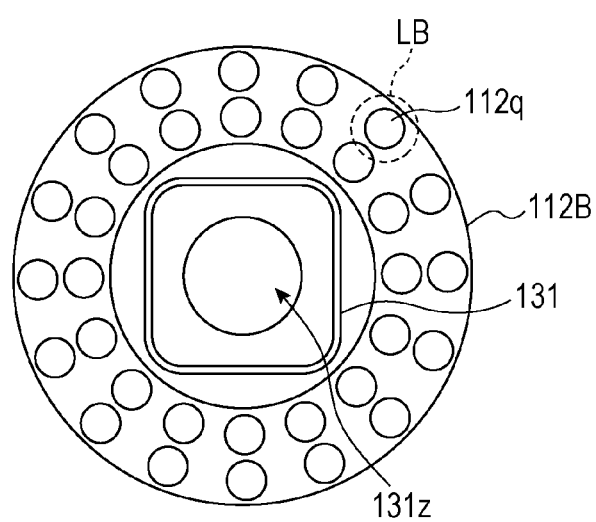
FIG. 9 is a view for explaining an exemplary configuration of a second illuminating unit of the lighting device and is a plan view of the second illuminating unit when viewed along an optical axis of an objective lens.

FIG. 9 illustrates the second illuminating unit 112B viewed along the optical axis Lz of the objective lens 131z. As illustrated in FIG. 9, the plurality of light emitting units LB, i.e., the plurality of light sources 112q are disposed in a ring shape so as to surround the objective lens 131z of the camera unit 131.

Figure 10:
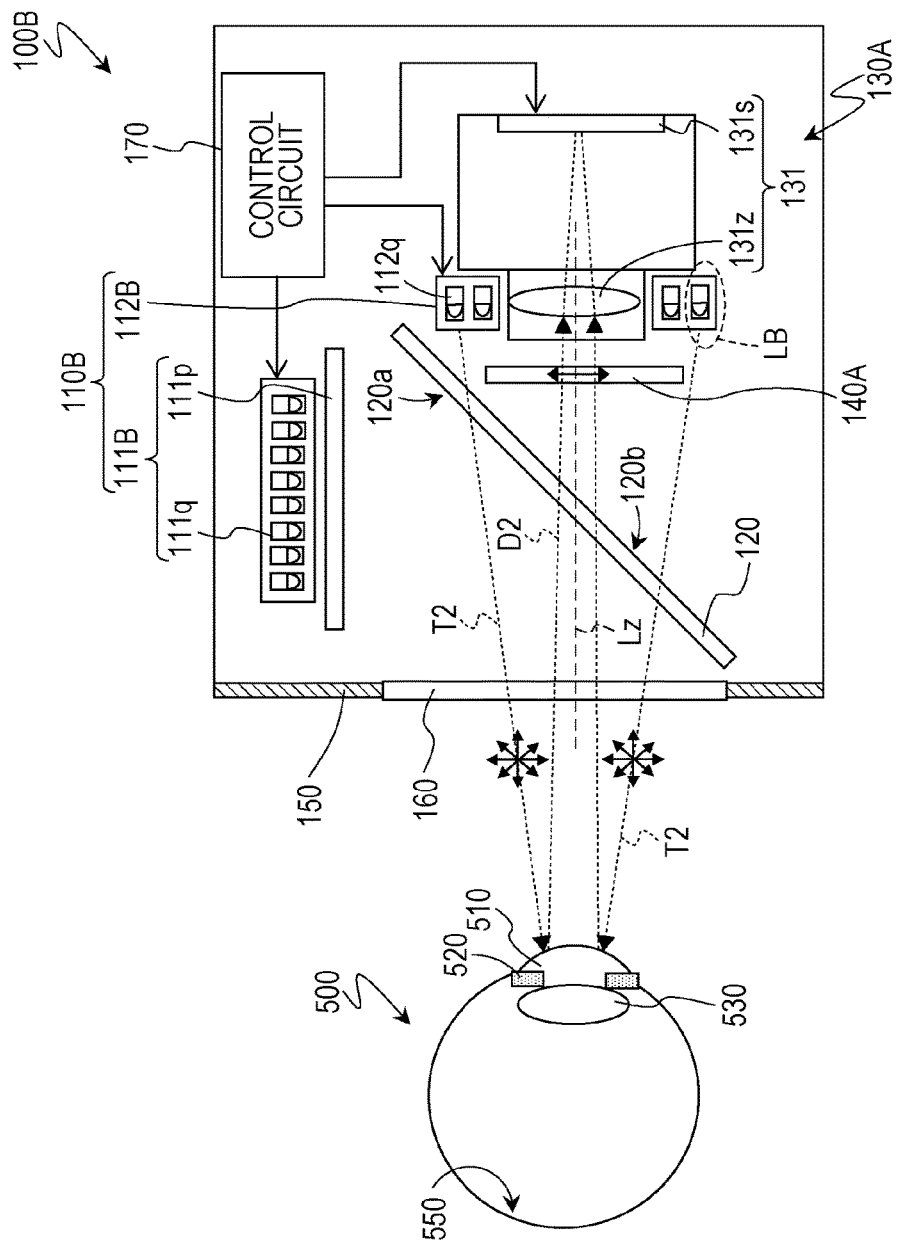
FIG. 10 is a view for explaining an exemplary configuration of the eye imaging apparatus according to the first modification of First Embodiment and an operation in the cornea imaging mode.

FIG. 10 is a view for explaining an operation of the eye imaging apparatus 100B in the cornea imaging mode. In the cornea imaging mode, the control circuit 170 turns on the plurality of light sources 112q of the second illuminating unit 112B and turns off the plurality of light sources 111q of the first illuminating unit 111B. Light emitted from the light emitting units LB (the plurality of light sources 112q in this case) of the second illuminating unit 112B passes through the half mirror 120 from the second surface 120b side to the first surface 120a side and travels toward the eye 500. Since the plurality of light emitting units LB are disposed so as to surround the objective lens 131z, transmitted light T2 (unpolarized light in this case) that has passed through the half mirror 120 enters the eye 500 from directions different from a direction parallel with the optical axis Lz, as schematically illustrated in FIG. 10. Light reflected by the cornea 510 of the eye 500 travels toward the camera unit 131 as return light D2 and forms an image concerning the cornea of the eye 500. In this way, the second illuminating unit 112B may emit light that passes through the half mirror 120 and travels toward the eye 500.

Figure 11:
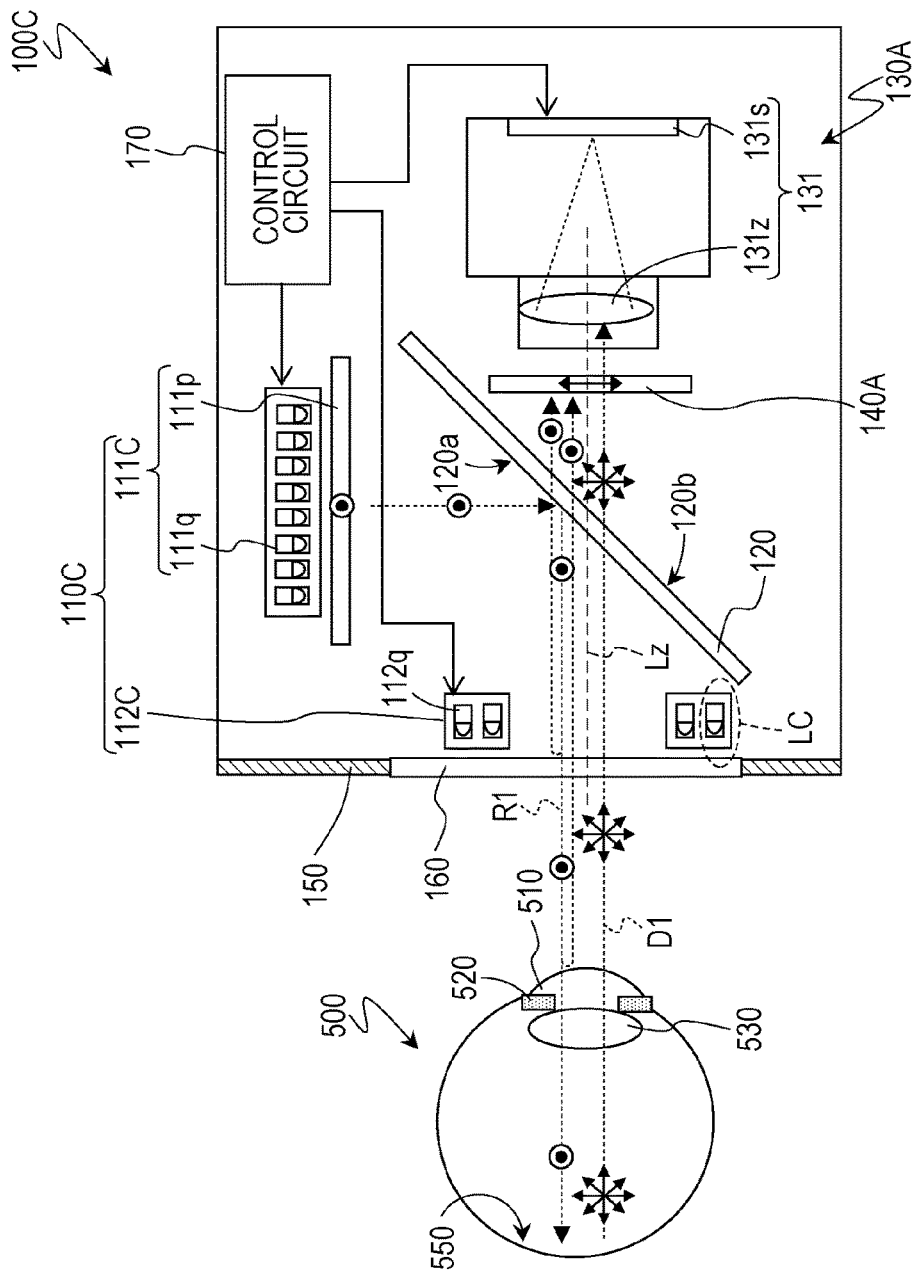
FIG. 11 is a view for explaining an exemplary configuration of an eye imaging apparatus according to a second modification of First Embodiment and an operation in the fundus imaging mode.
Figure 12:
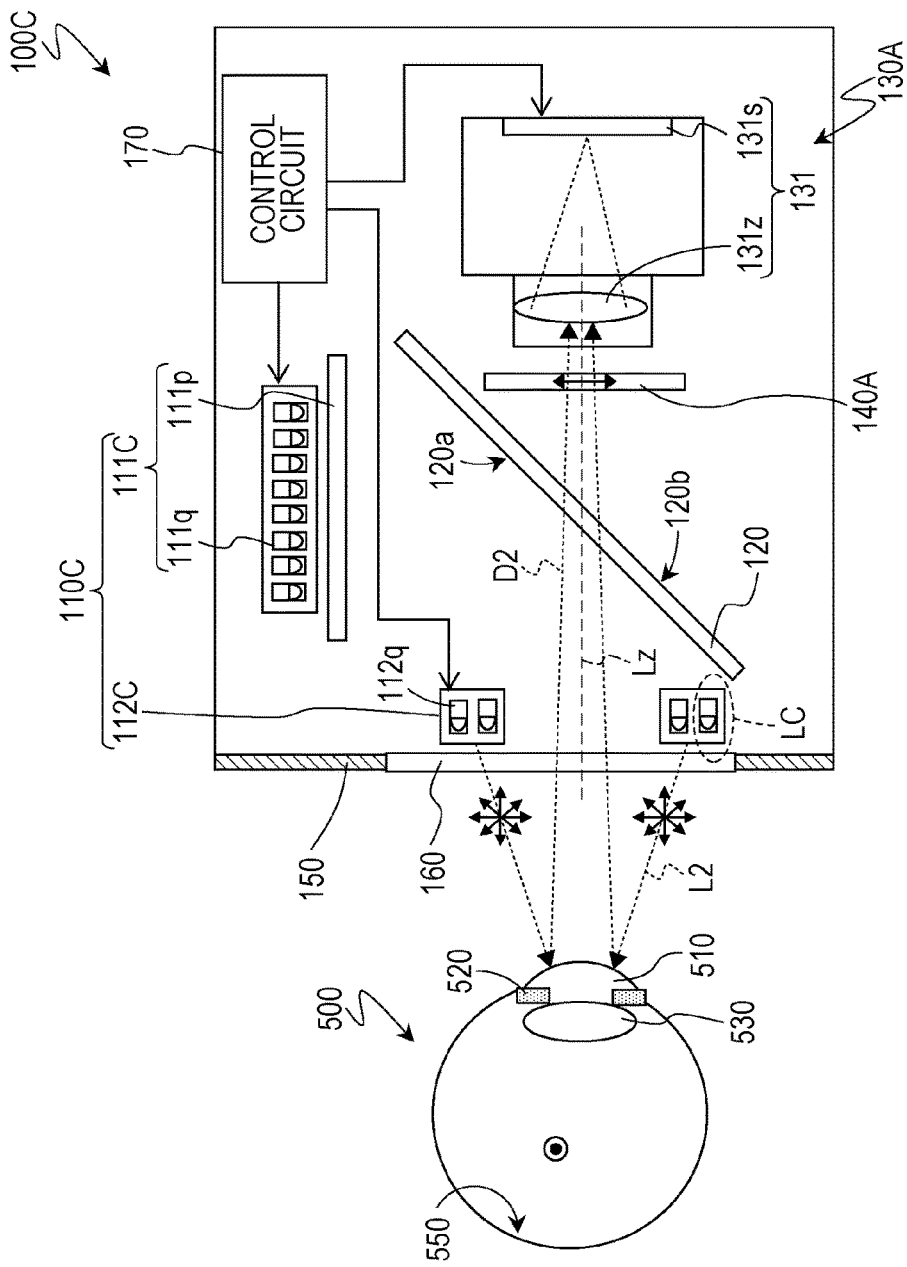
FIG. 12 is a view for explaining an exemplary configuration of the eye imaging apparatus according to the second modification of First Embodiment and an operation in the cornea imaging mode.

FIGS. 11 and 12 illustrate a second modification of the eye imaging apparatus. An eye imaging apparatus 100C illustrated in FIGS. 11 and 12 includes a lighting device 110C including a first illuminating unit 111C and a second illuminating unit 112C. As in the first modification, the second illuminating unit 112C is disposed separately from the first illuminating unit 111C in the eye imaging apparatus 100C.

FIGS. 11 and 12 schematically illustrate an operation of the eye imaging apparatus 100C in the fundus imaging mode and an operation of the eye imaging apparatus 100C in the cornea imaging mode. First, see FIG. 11. The operation of the eye imaging apparatus 100C in the fundus imaging mode is similar to the operation of the eye imaging apparatuses 100A and 100B in the fundus imaging mode. The first illuminating unit 111C of the lighting device 110C irradiates a first surface 120a of a half mirror 120 with linearly-polarized light, and the half mirror 120 reflects, toward an eye 500, reflected light R1 that travels in a direction that is in alignment with an optical axis Lz of an objective lens 131z. The first illuminating unit 111C can have a configuration similar to the configuration (see FIG. 8) of the first illuminating unit 111B in the first modification.

See FIG. 12. In this example, the second illuminating unit 112C is located on a side of the half mirror 120 opposite to a side on which a camera unit 131 is located, i.e., between a light transmitting part 160 and the first surface 120a of the half mirror 120, as schematically illustrated in FIG. 12. The second illuminating unit 112C includes a plurality of light emitting units LC. These light emitting units LC are disposed around the optical axis Lz of the objective lens 131z so as not to overlap the objective lens 131z. The way in which the plurality of light emitting units LC are disposed when viewed along the optical axis Lz of the objective lens 131z is almost similar to the way in which the light emitting units LB of the second illuminating unit 112B described with reference to FIG. 9 are disposed, and therefore illustration thereof is omitted.

According to such a configuration, the eye 500 can be irradiated, from directions different from a direction parallel with the optical axis Lz, with light L2 (typically unpolarized light) that is emitted from the light emitting units LC of the second illuminating unit 112C and passed through the light transmitting part 160. According to the configuration illustrated in FIGS. 11 and 12, independency of the first illuminating unit 111C and the second illuminating unit 112C is higher, and it is easier to design a lighting optical system. According to the configuration illustrated in FIGS. 11 and 12, the eye 500 can be irradiated with unpolarized light without intervention of the half mirror 120. This makes it possible to prevent unnecessary specular reflection by the half mirror 120 and to reduce the area of the half mirror 120, as compared with the second modification. Furthermore, since the plurality of light emitting units LC are located closer to the eye 500, the eye 500 can be irradiated at a larger incident angle.

Figure 13:
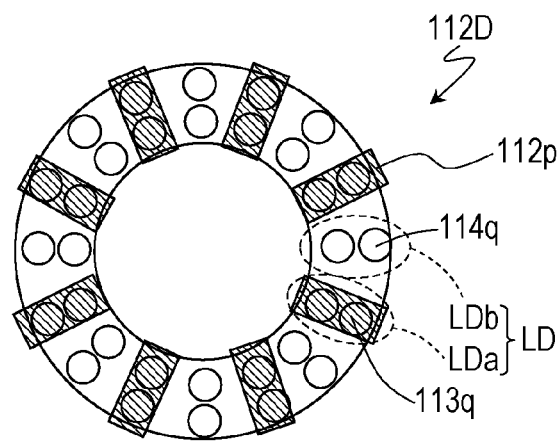
FIG. 13 is a plan view illustrating a second illuminating unit of a lighting device according to a third modification of the eye imaging apparatus.

FIG. 13 illustrates a third modification of the eye imaging apparatus. In FIG. 13, a second illuminating unit 112D of a lighting device is illustrated. A configuration similar to the configurations in the above examples can be applied as a configuration of the other part of the eye imaging apparatus. For example, any of the first illuminating units 111A through 111C may be employed as a first illuminating unit.

The second illuminating unit 112D illustrated in FIG. 13 includes a plurality of light emitting units LD including light emitting units LDa and light emitting units LDb. As illustrated in FIG. 13, the plurality of light emitting units LD are disposed, for example, in a ring shape. The light emitting units LD can be disposed so as to surround the first illuminating unit as in the configuration described with reference to FIG. 2. Alternatively, the light emitting units LD can be disposed so as to surround an objective lens 131z as in the configuration described with reference to FIG. 9. The second illuminating unit 112D may be disposed on a second surface 120b side of a half mirror 120 as in the example described with reference to FIGS. 7 and 10 or may be disposed on a first surface 120a side of the half mirror 120 as in the example described with reference to FIGS. 11 and 12.

In the configuration illustrated in FIG. 13, the light emitting units LDa and the light emitting units LDb are alternately disposed along a circle. The light emitting units LDa includes a plurality of light sources 113$q$ and a plurality of polarizers 112$p$ that cover the plurality of light sources 113$q$. A direction orthogonal to a transmission axis of a polarizer 140A disposed in front of a camera unit 131 is selected as a direction of a transmission axis of each of the plurality of polarizers 112$p$, as in the case of the polarizer 111$p$. Meanwhile, the light emitting units LDb have a plurality of light sources 114$q$, and no polarizer is disposed in front of the plurality of light sources 114$q$. In a case where the second illuminating unit 112D having a such a configuration is applied, the plurality of light sources 113$q$ of the light emitting units LDa and the plurality of light sources 114$q$ of the light emitting units LDb are controlled to emit light at respective different timings, for example, on the basis of an instruction from the control circuit 170 in the cornea imaging mode.

Figure 14:
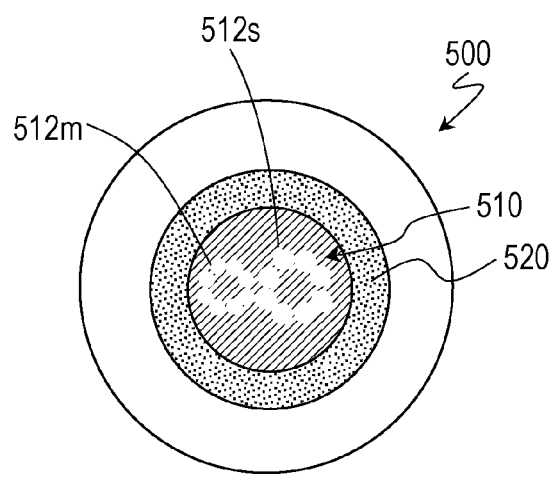

FIG. 14 illustrates an example of an image of an eye obtained in a state where the plurality of light sources 114$q$ of the light emitting units LDb are on and the plurality of light sources 113$q$ of the light emitting units LDa are off. However, a plurality of light sources of the first illuminating unit are off. Since no polarizer is disposed in front of the plurality of light sources 114$q$, a ring-shaped bright part 512$m$ appears in the image in a background of a dark pupil due to return light generated after multiple reflection in the eye 500, and a ring-shaped bright part 512$s$ also appears in the image due to specular reflection on a surface of the cornea 510 and vicinity thereof in a state where the plurality of light sources 114$q$ are selectively on, as in the example described with reference to FIG. 6.

Figure 15:
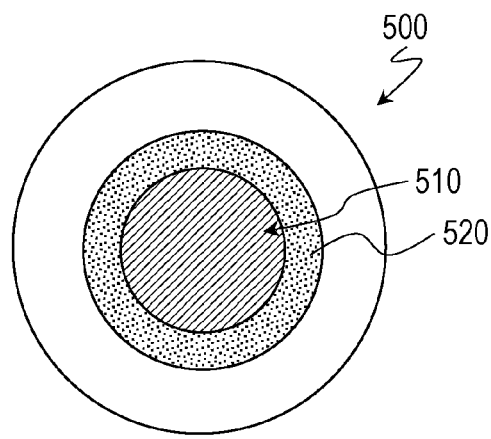

FIG. 15 illustrates an example of an image of an eye obtained in a state where the plurality of light sources 113$q$ of the light emitting units LDa are on and the plurality of light sources 114$q$ of the light emitting units LDb are off. However, the plurality of light sources of the first illuminating unit are off. The light emitting units LDa include the plurality of polarizers 112$p$ disposed in front of the plurality of light sources 113$q$. Accordingly, the eye 500 is irradiated with linearly-polarized light in a state where the plurality of light sources 113$q$ are selectively on. Since a direction orthogonal to the transmission axis of the polarizer 140A is selected as a direction of a transmission axis of each of the plurality of polarizers 112$p$, return light generated after multiple reflection in the eye 500 and return light generated by specular reflection on the surface of the cornea 510 and vicinity thereof are blocked by the polarizer 140A. As a result, the bright parts 512m and 512s illustrated in FIG. 14 do not appear in an image of an eye obtained in a state where the plurality of light sources 113q of the light emitting units LDa are selectively on.

By thus providing, in a second illuminating unit that offers light for lighting a cornea, two types of light emitting units, one of which is a light emitting unit that provides unpolarized light, and the other one of which is a light emitting unit that provides linearly-polarized light having an electric field vector that oscillates in a direction orthogonal to the transmission axis of the polarizer 140A, it is possible to obtain two types of images concerning the cornea. It can be said that the mode in which the eye is imaged while selectively turning on the plurality of light sources 114q of the light emitting units LDb is a mode for generating specular reflection on the cornea and obtaining an image generated by the specular reflection.

According to such a mode, an irregularity, a foreign substance, or a scratch on the surface of the cornea can be easily detected. Meanwhile, it can be said that the mode in which the eye is imaged while selectively turning on the plurality of light sources 113q of the light emitting units LDa is a mode in which influence of return light generated by specular reflection on the surface of the cornea and vicinity thereof is removed. According to such a mode, an image useful for observation of scattering of light by aqueous humor directly below the cornea (in an anterior eye chamber), a crystalline lens, or the like and clouding of the crystalline lens can be obtained, and therefore such a mode is useful for diagnosis of cataract and other diseases.

According to the configuration in which the mode can be switched between the mode in which an image of return light generated by specular reflection on the surface of the cornea and vicinity thereof can be observed and the mode in which influence of return light generated by specular reflection is removed, an image that provides more useful information can be obtained according to a purpose. Note that the way in which the light emitting units LDa and LDb are disposed is not limited to that described with reference to FIG. 13 in which the light emitting units LDa and LDb are disposed along a circle. However, the configuration in which the light emitting units LDa and LDb are alternately disposed along a circle is advantageous from a perspective of causing light to enter the cornea at the same incident angle in both of the two modes.

Second Embodiment

Figure 16:
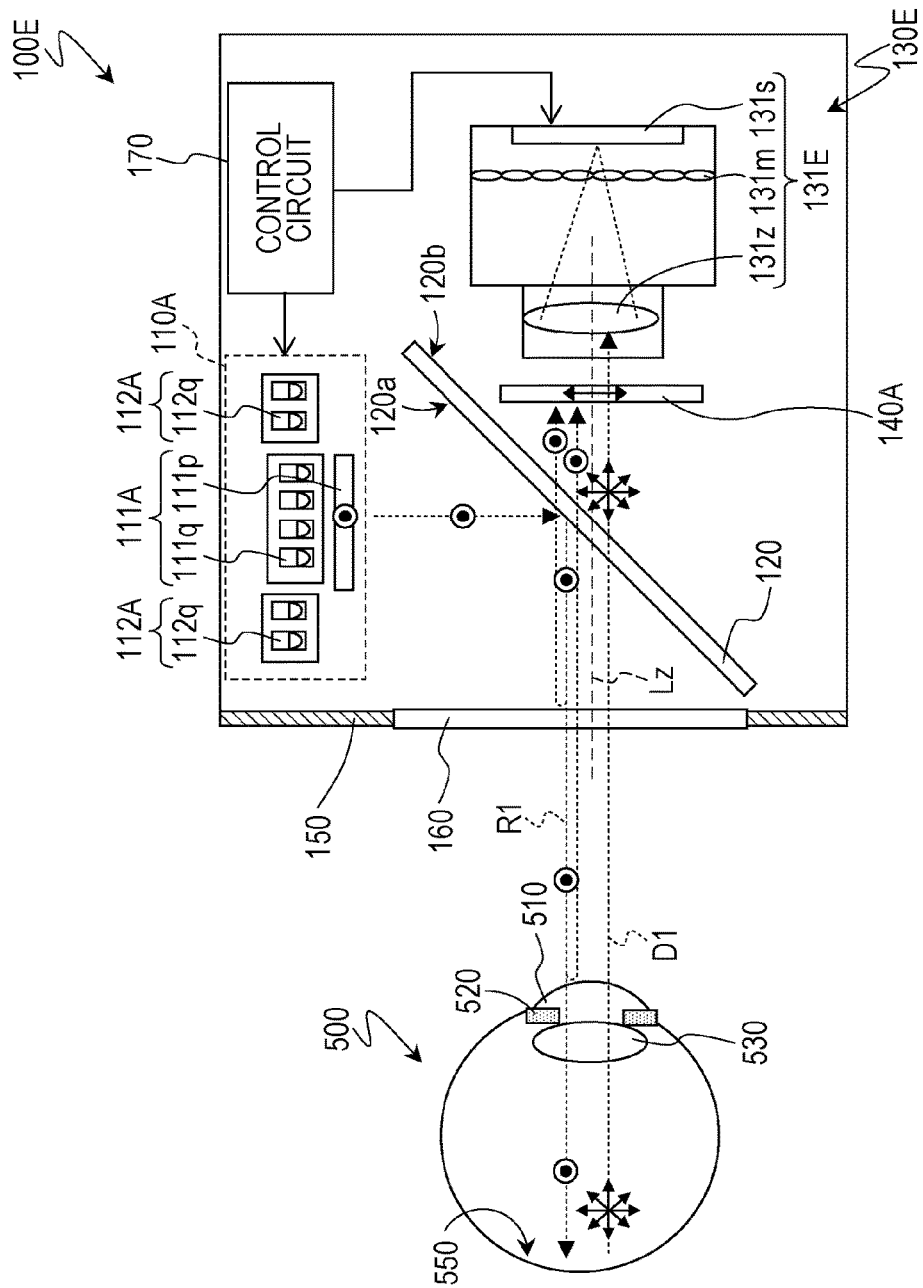
FIG. 16 is a view for explaining an exemplary configuration of an eye imaging apparatus according to Second Embodiment and an operation in a fundus imaging mode.
Figure 17:
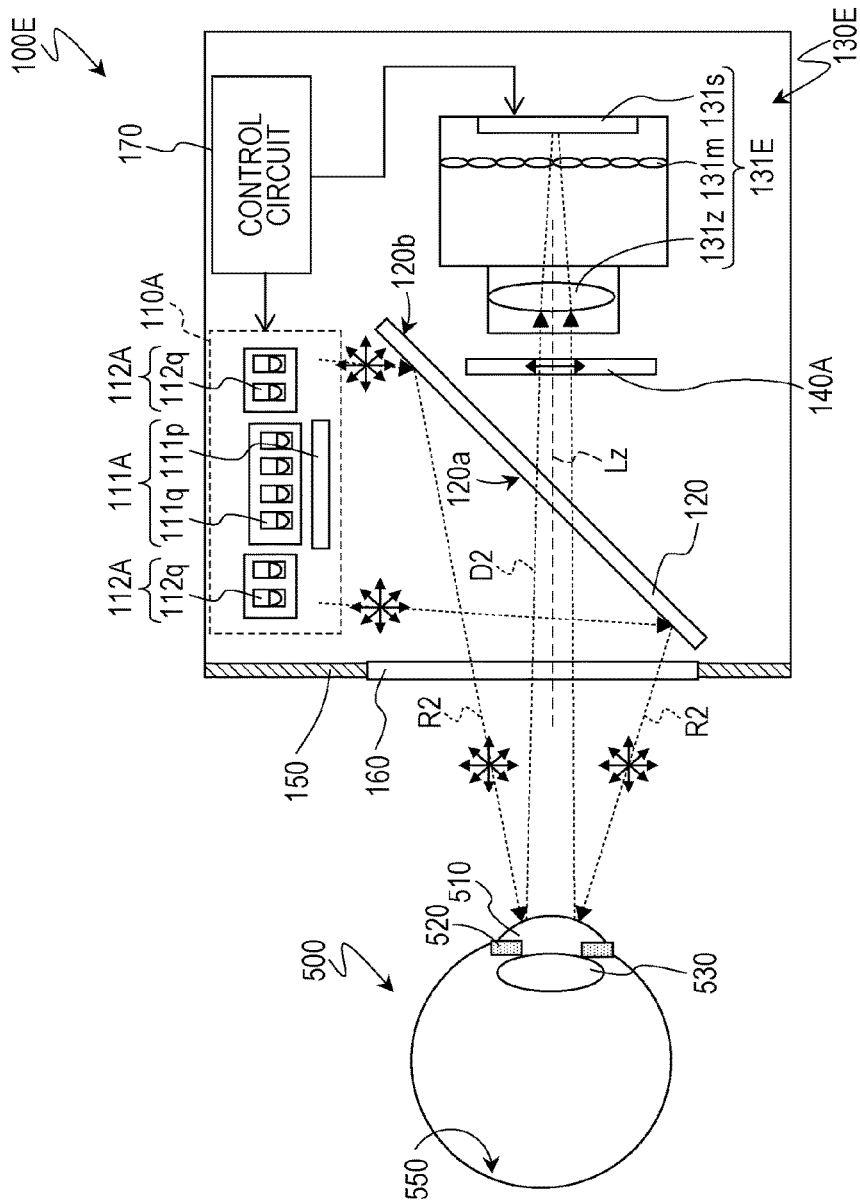
FIG. 17 is a view for explaining an exemplary configuration of the eye imaging apparatus according to Second Embodiment and an operation in a cornea imaging mode.

An imaging device of an eye imaging apparatus according to the present disclosure can also be modified in various ways, as in the case of a lighting device. FIGS. 16 and 17 schematically illustrate an exemplary configuration of an eye imaging apparatus according to Second Embodiment of the present disclosure. The eye imaging apparatus 100E illustrated in FIGS. 16 and 17 includes an imaging device 130E instead of the imaging device 130A as compared with the eye imaging apparatus 100A described with reference to FIG. 1.

The imaging device 130E is a light field camera. The imaging device 130E includes a microlens array 131m disposed between an objective lens 131z and an image sensor 131s and is configured so that focus is adjustable after image data is obtained. The microlens array 131m includes a plurality of microlenses, and each of the plurality of microlenses covers a region including a plurality of imaging cells of the image sensor 131s. Use of the microlens array 131m allows the image sensor 131s to record, for each incident angle, an image formed by a light beam that has passed through the objective lens 131z. This makes it possible to generate an image focused at a different distance afterward on the basis of obtained image data by performing image processing on the obtained image data even in a case where the number of times of imaging is one. An imaging device that can be refocused after image data is obtained is sold, for example, by Lytro, Inc. by the name of ILLUM (Registered Trademark).

FIGS. 16 and 17 schematically illustrate an operation of the eye imaging apparatus 100E in a fundus imaging mode and an operation of the eye imaging apparatus 100E in a cornea imaging mode, respectively. In the fundus imaging mode, an eye 500 is imaged by the imaging device 130E including a camera unit 131E configured as a light field camera in a state where a plurality of light sources 111q of a first illuminating unit 111A are on and a plurality of light sources 112q of a second illuminating unit 112A are off. A refocused image is generated as needed on the basis of obtained image data. The refocused image may be generated by a control circuit 170 or may be generated by an external device connected to the eye imaging apparatus 100E. By applying an imaging device configured to be refocused, an image containing a highest-frequency component concerning texture can be selected from among images concerning a fundus by virtually changing focus without measuring a distance between the fundus 550 of the eye 500 and an imaging surface of the image sensor 131s in advance. That is, a clear image concerning the fundus 550 can be obtained with more certainty. It is therefore possible to more effectively inspect, for example, a blood vessel and a nerve in the retina.

In the cornea imaging mode, the eye 500 is imaged in a state where the plurality of light sources 112q of the second illuminating unit 112A are on and the plurality of light sources 111q of the first illuminating unit 111A are off. A refocused image is generated as needed on the basis of image data obtained by the imaging device 130E. For example, an image containing a highest-frequency component is generated from images in which a bright spot generated by specular reflection on the cornea 510 appears. By generating an image focused on the position of the cornea 510, a clear image concerning the surface of the cornea 510 can be obtained. This is advantageous, for example, for inspection of a scratch on a cornea.

By applying an imaging device that can be refocused, a clear image concerning a fundus and/or a cornea can be obtained even in a case where a distance between a subject and a camera cannot be fixed and an opportunity to image the subject is a brief moment. The above configuration is advantageous especially for obtaining an image concerning an eye of a subject without subject's awareness (sometimes called casual sensing of an eye).

Modifications of Second Embodiment

Figure 18:
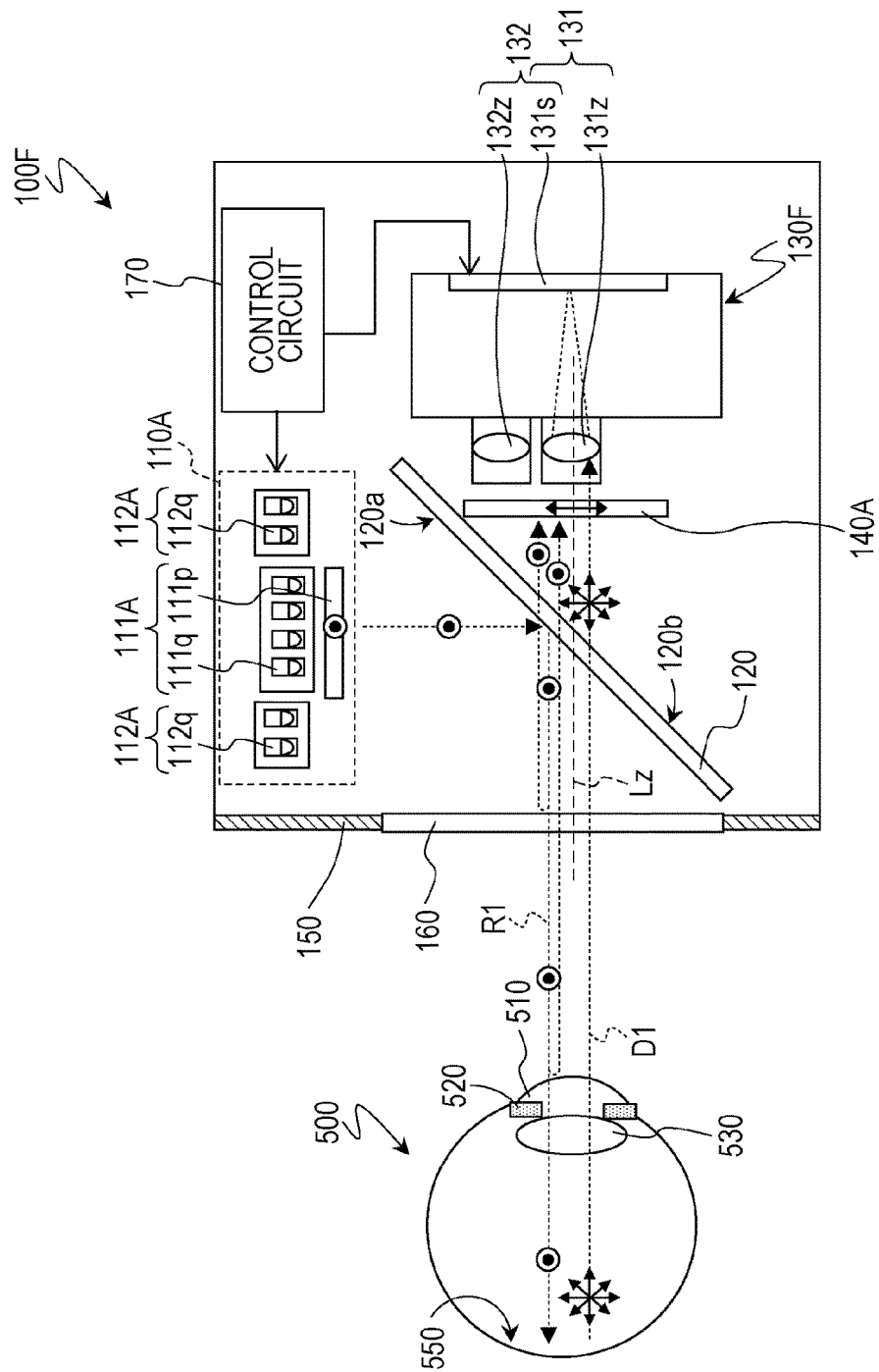
FIG. 18 is a view for explaining an exemplary configuration of an eye imaging apparatus according to a fourth modification and an operation in the fundus imaging mode.
Figure 19:
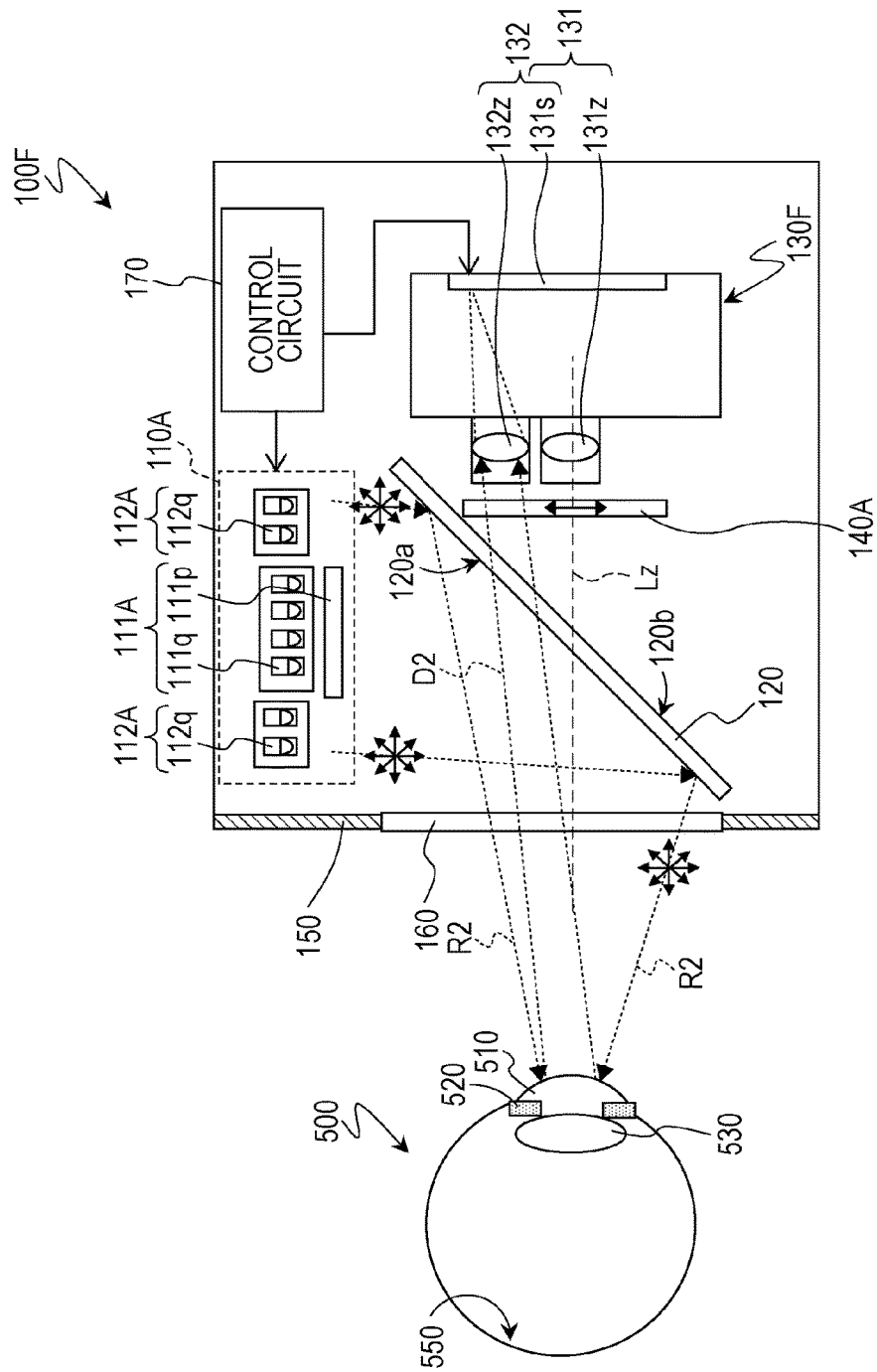
FIG. 19 is a view for explaining an exemplary configuration of the eye imaging apparatus according to the fourth modification and an operation in the cornea imaging mode.

FIGS. 18 and 19 illustrate a fourth modification of the eye imaging apparatus. An eye imaging apparatus 100F illustrated in FIGS. 18 and 19 includes an imaging device 130F including a first camera unit 131 and a second camera unit 132. In the configuration illustrated in FIGS. 18 and 19, the second camera unit 132 includes an objective lens 132z and an image sensor 131s. That is, in this example, the first camera unit 131 and the second camera unit 132 share the image sensor 131s. Alternatively, the first camera unit 131 and the second camera unit 132 each may have an independent image sensor. In this example, the camera unit 132 is covered with a polarizer 140A when viewed along an optical axis Lz of an objective lens 131z, as schematically illustrated in FIGS. 18 and 19.

FIG. 18 schematically illustrates an operation of the eye imaging apparatus 100F in a fundus imaging mode. In the fundus imaging mode, a control circuit 170 causes the image sensor 131s to obtain an image concerning a fundus 550 by turning on a plurality of light sources 111q of a first illuminating unit 111A, turning off a plurality of light sources 112q of a second illuminating unit 112A, and causing the camera unit 131 to operate in synchronization with turning on of the plurality of light sources 111q, as has been described above.

FIG. 19 schematically illustrates an operation of the eye imaging apparatus 100F in a cornea imaging mode. As in the above examples, the plurality of light sources 112q of the second illuminating unit 112A are turned on, the plurality of light sources 111q of the first illuminating unit 111A are turned off, and an image concerning a cornea 510 is obtained by the image sensor 131s in synchronization with turning on of the plurality of light sources 112q. However, in this example, an image concerning the cornea 510 is obtained by the camera unit 132. In other words, the image concerning the cornea 510 is an image formed by a light beam that has passed through the objective lens 132z of the camera unit 132.

Focus of the camera units 131 and 132 is typically fixed. Assume that the same eye 500 is imaged without changing a relative positional relationship between the eye imaging apparatus 100F and the eye 500, the cornea 510 of the eye 500 is located closer to the eye imaging apparatus 100F than the fundus 550. That is, in a case where the cornea 510 is imaged, a clearer image concerning the cornea 510 can be obtained by focusing on a position closer to the apparatus, as compared with a case where the fundus 550 is imaged.

In this example, a lens having a shorter focal length than the objective lens 131z of the camera unit 131 is used as the objective lens 132z of the camera unit 132. This makes it easier to focus on the cornea 510 and to more clearly image, for example, light generated by specular reflection on a surface of the cornea 510 even in a case where the fundus imaging mode and the cornea imaging mode are switched at relatively short intervals. According to such a configuration in which an objective lens to be used in switched between objective lenses having different focal lengths in accordance with which of a fundus and a cornea is to be imaged, it is possible to obtain an image focused on the fundus and an image focused on the cornea with more certainty. The objective lens 131z is not limited to a single lens and may be a combination of one or more lenses. The same applies to the objective lens 132z.

Figure 20:
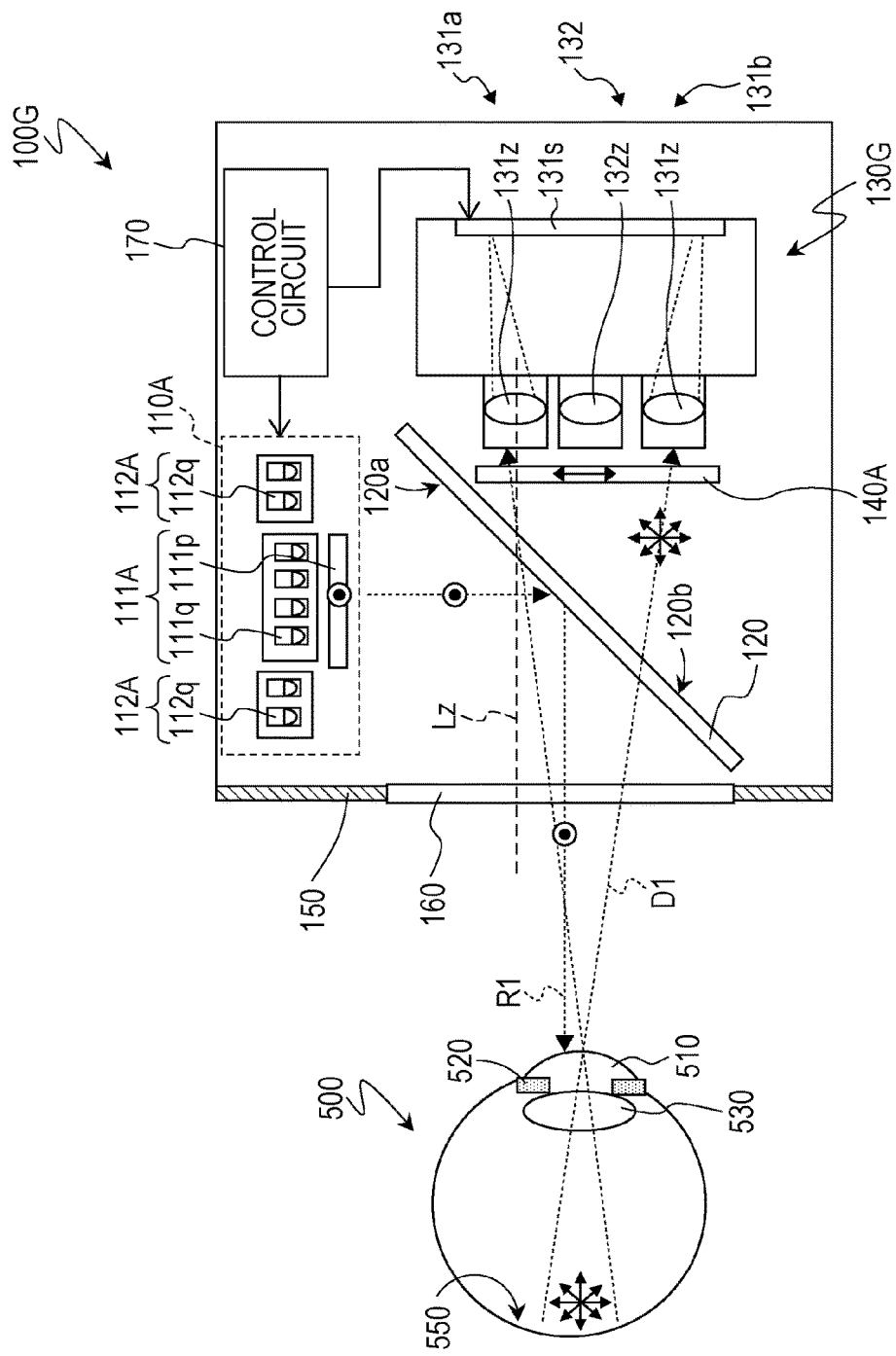
FIG. 20 is a view for explaining an exemplary configuration of an eye imaging apparatus according to a fifth modification and an operation in the fundus imaging mode.
Figure 21:
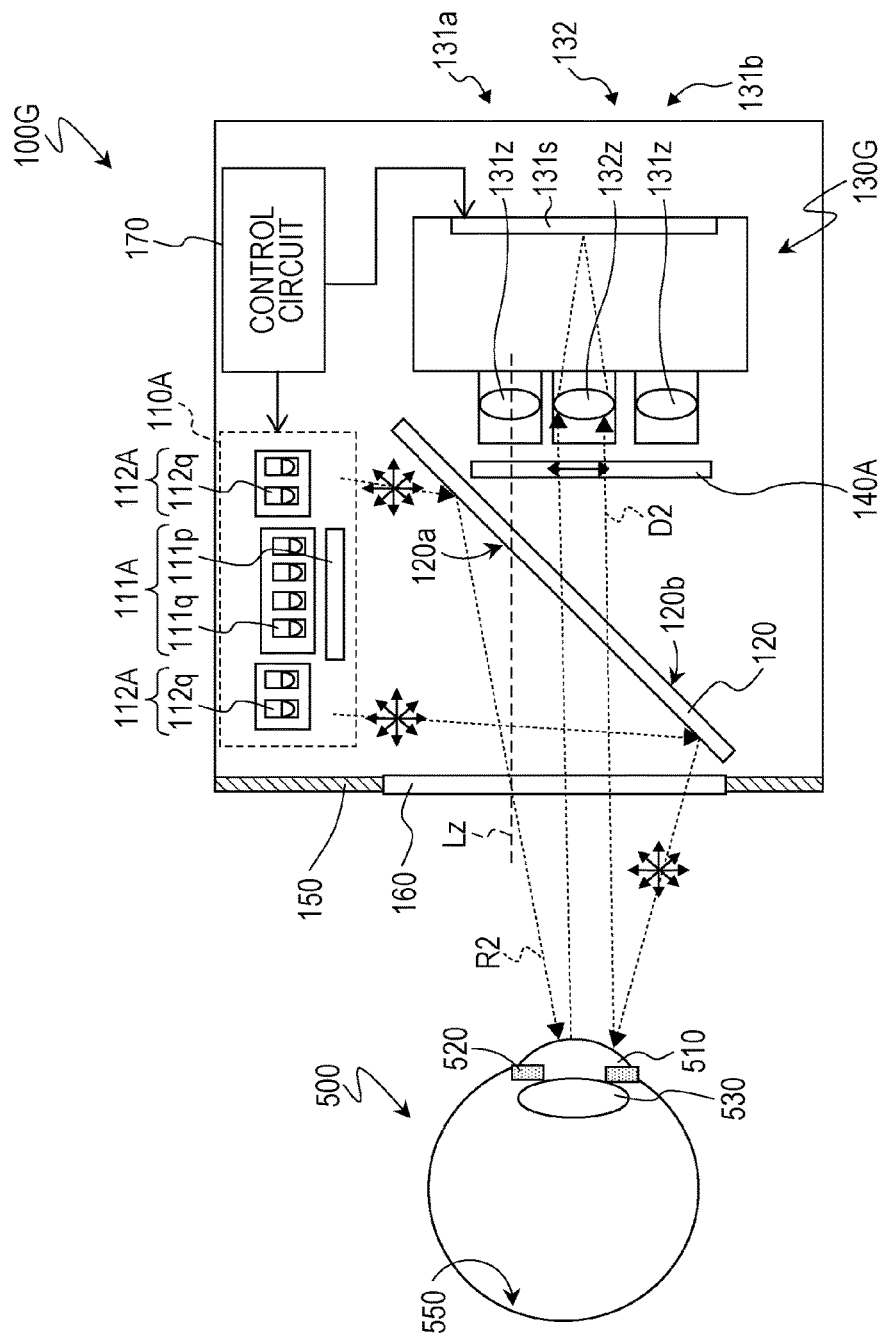
FIG. 21 is a view for explaining an exemplary configuration of the eye imaging apparatus according to the fifth modification and an operation in the cornea imaging mode.

FIGS. 20 and 21 illustrate an exemplary configuration of an eye imaging apparatus 100G according to a fifth modification. FIGS. 20 and 21 schematically illustrate an operation of the eye imaging apparatus 100G in a fundus imaging mode and an operation of the eye imaging apparatus 100G in a cornea imaging mode.

The eye imaging apparatus 100G illustrated in FIGS. 20 and 21 is the same as the imaging device 130F described with reference to FIGS. 18 and 19 in that the eye imaging apparatus 100G includes an imaging device 130G including a second camera unit 132. The eye imaging apparatus 100G illustrated in FIGS. 20 and 21 is different from the eye imaging apparatus 100F described with reference to FIGS. 18 and 19 in that the imaging device 130G of the eye imaging apparatus 100G includes a plurality of first camera units. In the example illustrated in FIGS. 20 and 32, a camera unit 131a including an objective lens 131z and a camera unit 131b including an objective lens 131z are disposed on an upper side and a lower side of the camera unit 132, respectively. The plurality of first camera units include the camera unit 131a and the camera unit 131b.

Figure 22:
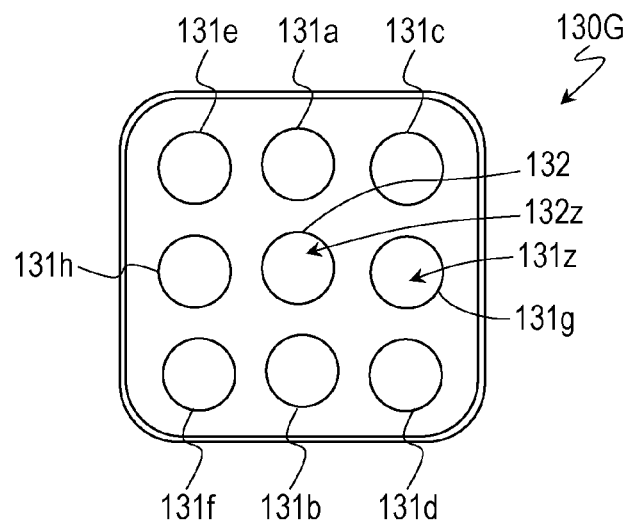
FIG. 22 is a plan view illustrating an example of a way in which camera units are disposed when viewed along an optical axis of an objective lens.

FIG. 22 illustrates an example of the way in which the camera units are disposed when viewed along an optical axis Lz of the objective lens 131z. In the configuration illustrated in FIG. 22, the imaging device 130G includes first camera units 131a through 131h each including the objective lens 131z and the second camera unit 132 disposed at a center of the imaging device 130G. As illustrated in FIG. 22, the objective lenses 131z of the first camera units 131a through 131h are disposed so as to surround the objective lens 132z of the second camera unit 132. In the example illustrated in FIG. 22, these objective lenses are arranged in a matrix of three rows and three columns. A center-to-center distance between two objective lenses that are adjacent in a row direction or a column direction can be approximately 1 mm to 2 mm.

In this example, an image concerning a cornea of an eye is obtained by the second camera unit 132, and a plurality of images concerning a fundus of the eye are obtained by the plurality of first camera units 131a through 131h. Therefore, typically, a focal length of the objective lens 132z of the camera unit 132 is shorter than a focal length of the objective lenses 131z of the camera units 131a through 131h.

See FIG. 20 again. As schematically illustrated in FIG. 20, in a fundus imaging mode, an eye 500 is irradiated with reflected light R1 of linearly-polarized light. Each of the first camera units 131a through 131h obtains image data concerning a fundus 550 on the basis of return light D1 from the fundus 550. That is, in this example, eight images in total are obtained by one imaging. In this example, since the first camera units 131a through 131h share a single image sensor 131s, the camera units are configured so that light that has passed through the objective lenses 131z forms images in different regions on an imaging surface of the image sensor 131s. Meanwhile, in a cornea imaging mode, the eye 500 is irradiated with reflected light R2 of unpolarized light, and the second camera unit 132 obtains image data concerning the cornea 510 on the basis of return light D2 from the cornea 510, as schematically illustrated in FIG. 21.

Figure 23:
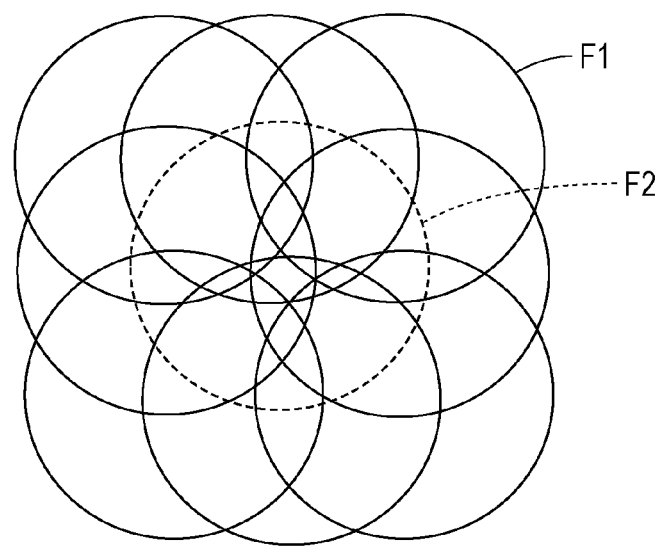
FIG. 23 schematically illustrates a combination of view fields obtained by camera units and a view field of a camera unit.

FIG. 23 schematically illustrates a combination of fields of view of the camera units 131a through 131h and a field of view of the camera unit 132. In FIG. 23, the broken-line circle F2 schematically indicates the field of view of the camera unit 132. The camera unit 132 images a center of a pupil of the eye 500 and surroundings thereof. In FIG. 23, the solid-line circles F1 schematically indicate the fields of view of the camera units 131a through 131h. The plurality of circles F1 overlap one another. It is therefore possible to obtain an image of a larger field of view concerning the fundus 550 by synthesizing eight images obtained by the camera units 131a through 131h. That is, it is possible to observe a wider region of the fundus 550 on the basis of the images obtained by the eye imaging apparatus 100G.

In general, it is difficult to obtain a wide field of view by one imaging since a fundus is imaged through a small pupil. Meanwhile, according to the fifth modification, a larger field of view can be realized by collectively obtaining images of a fundus from different directions by using a plurality of camera units and synthesizing these images. According to such a configuration, a larger field of view can be realized without bringing the apparatus to a distance of approximately 5 cm to an eye unlike a conventional apparatus. Since lighting of a first illuminating unit is close to coaxial lighting, it is unnecessary to image an eye while bringing the apparatus close to the eye unlike a conventional apparatus and it is therefore unnecessary to learn a special skill for imaging an eye.

Third Embodiment

Figure 24:
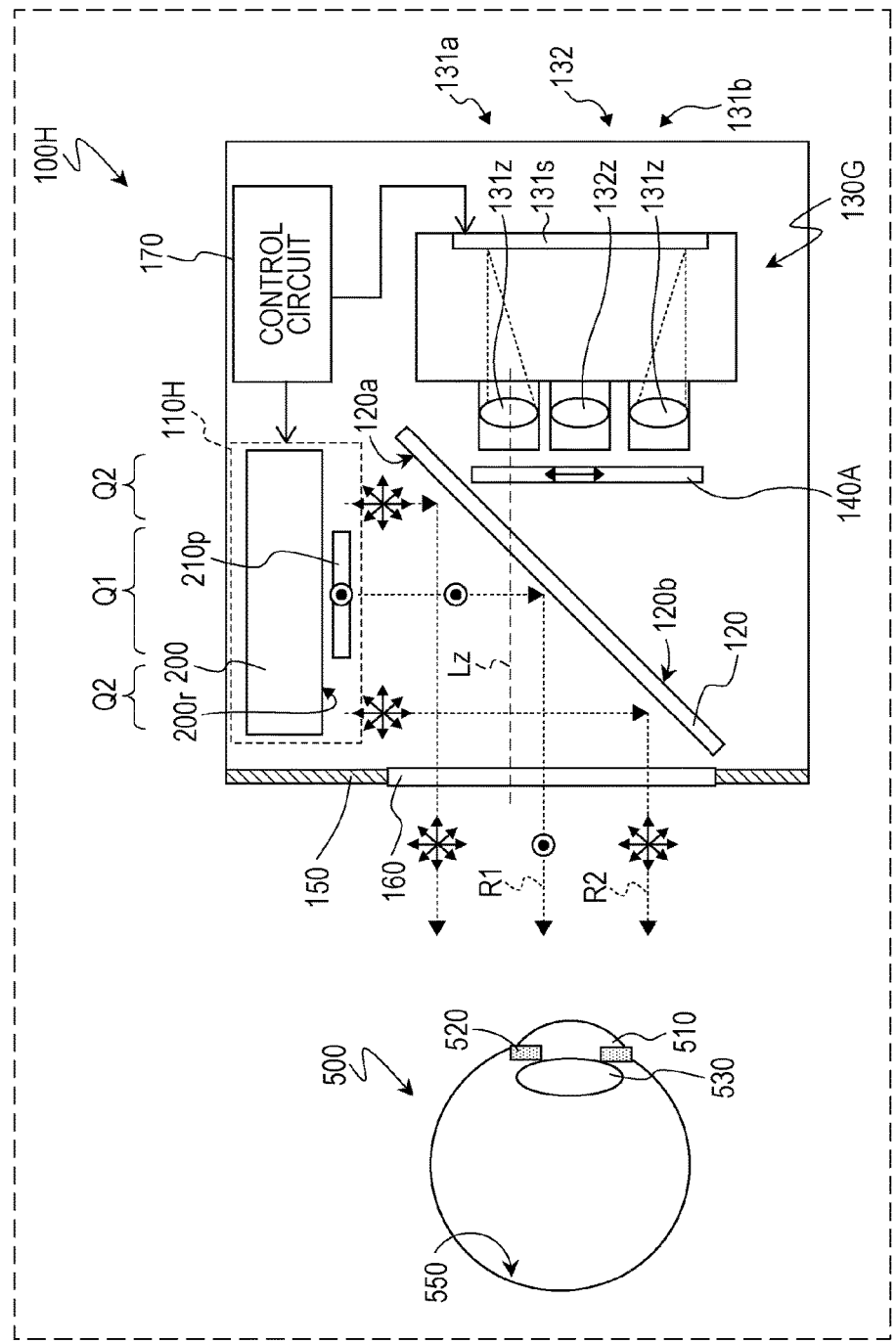
FIG. 24 schematically illustrates an exemplary configuration of an eye imaging apparatus according to Third Embodiment of the present disclosure.

FIG. 24 schematically illustrates an exemplary configuration of an eye imaging apparatus according to Third Embodiment of the present disclosure. An eye imaging apparatus 100H illustrated in FIG. 24 includes a lighting device 110H including a display 200 and a polarizer 210p. The display 200 has a display surface 200r, and the polarizer 210p covers a first region Q1 that is a central part of the display surface 200r. A second region Q2 around the first region Q1 of the display surface 200r is not covered with a polarizer. A transmission axis of the polarizer 210p disposed in front of the first region Q1 is orthogonal to a transmission axis of a polarizer 140A, for example, as in the case of the polarizer 111p of the first illuminating unit 111A of the lighting device 110A. A known display device can be used as the display 200. The following discusses an example in which the display 200 is an organic EI display (OELD). Although the imaging device 130G is applied in the configuration illustrated in FIG. 24, any of the imaging devices 130A, 130E, and 130F described above is also applicable.

The display 200 can display any image on the display surface 200r. Driving of the display 200 can be controlled, for example, by a control circuit 170. The control circuit 170 causes the imaging device 130G to sequentially obtain, for example, an image concerning a fundus 550 and an image concerning a cornea 510 by driving the display 200 and the imaging device 130G in synchronization with each other.

The eye imaging apparatus 100H can be mounted in a housing (e.g., behind a display unit) of a mobile tablet terminal, an electronic book reader, a gaming console, or the like. As is clear from FIG. 24, light from the display 200 is reflected by a half mirror 120 and then exits to an outside through a light transmitting part 160. In other words, a subject (hereinafter sometimes referred to as a user) who faces the eye imaging apparatus 100H can watch content such as an image displayed on the display 200. By inverting an image displayed on the display 200 as appropriate, the user is allowed to watch the image just like the user watches an image on a general terminal, thereby allowing the user to enjoy, for example, a game.

Figure 38A:
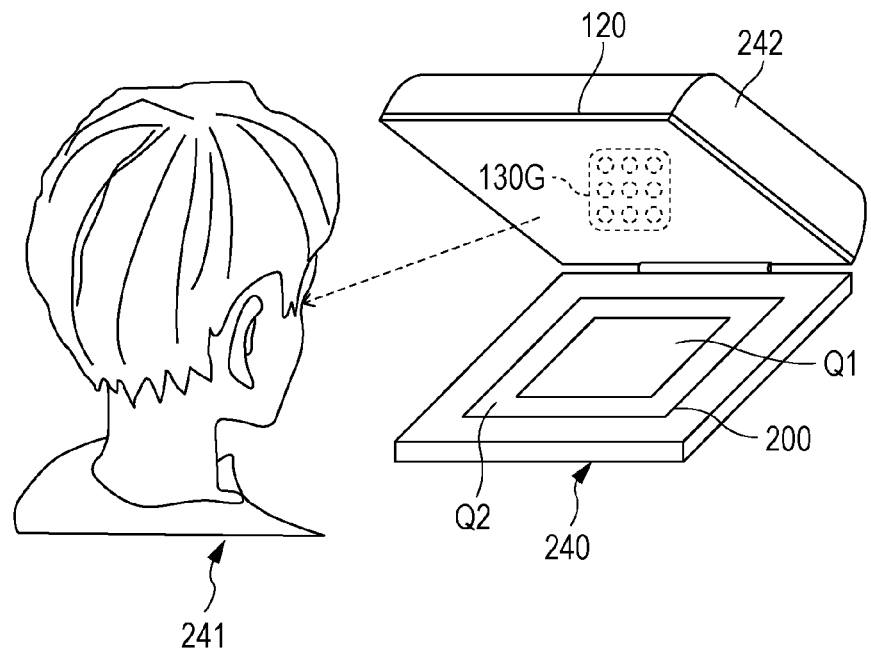
FIG. 38A is a perspective view of an example of a mobile tablet terminal.
Figure 38B:
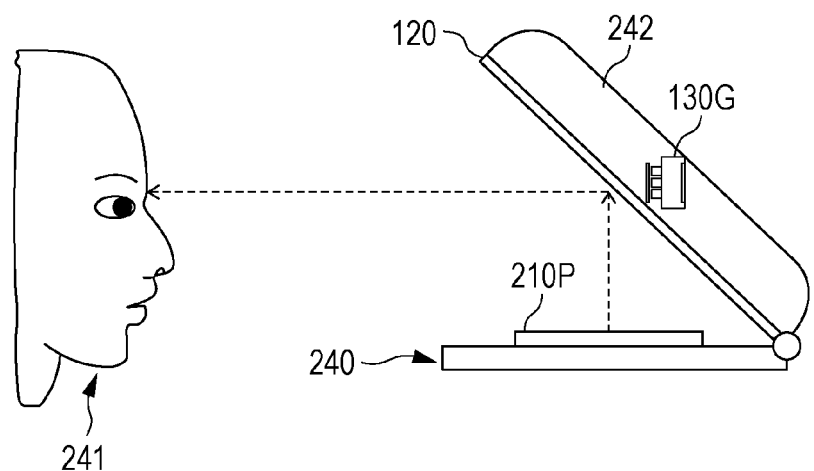
FIG. 38B is a side view of an example of a mobile tablet terminal.

FIGS. 38A and 38B are a perspective view and a side view of an example of a tablet terminal, respectively. The tablet terminal includes a tablet terminal body 240, a half mirror 120, a light shielding cover 242, and a display 200. The display 200 is disposed on a surface of the tablet terminal body 240.

The cover 242 has an opening. The half mirror 120 is disposed so as to cover the opening of the cover 242. The tablet terminal body 240 and the cover 242 are connected to each other with use of a hinge so that an angle defined by the tablet terminal body 240 and the half mirror 120 provided on the cover 242 can be changed. For example, the tablet terminal body 240 and the cover 242 can be fixed with the use of the hinge so that the angle defined by the display 200 and the half mirror 120 becomes 45 degrees.

The imaging device 130G is located in a space defined between the cover 242 and the half mirror 120. Although the light transmitting part 160 and a light shielding part 150 are omitted in FIGS. 38A and 38B, the light transmitting part 160 and the light shielding part 150 are also located in the space defined between the cover 242 and the half mirror 120.

The display 200 can be any display that can output unpolarized light and is, for example, an organic EL display. The display 200 has the central first region Q1 having a polarizer and the peripheral second region Q2 having no polarizer, and the first region Q1 and the second region Q2 are separated from each other. Content displayed on the display 200 is displayed across the first region Q1 and the second region Q2 and reaches eyes of a user 241 by being reflected by the half mirror 120 inclined by 45 degrees with respect to the display 200. The user 241 can play a game while watching a pseudo three-dimensional image by observing an image, such as content displayed on the display 200, reflected by the half mirror 120. Concurrently, healthcare check of the eyes in a fatigue state can be conducted by the imaging device 130G while changing the content displayed on the display 200.

The eye imaging apparatus 100H causes the display 200 to display content (e.g., an image or video including a text such as a website) desired by a user and images a user's eye at a certain timing. An example of an eye imaging operation performed by the eye imaging apparatus 100H is described below with reference to the drawings.

Figure 26A:
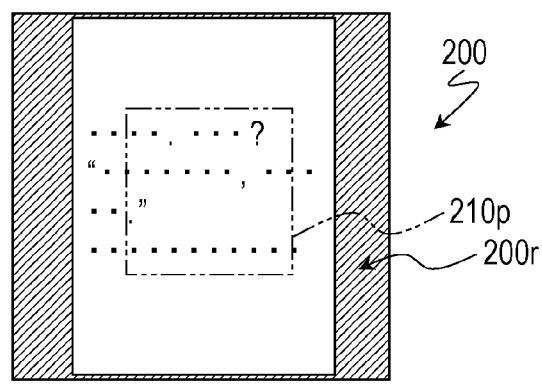
FIG. 26A is a view schematically illustrating an example of content displayed on a display.
Figure 26B:
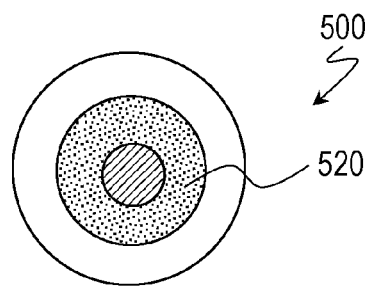
FIG. 26B is a view schematically illustrating how an eye of a user watching content displayed on the display looks.

FIG. 25 is a flowchart for explaining an example of an eye imaging operation performed by the eye imaging apparatus 100H. As illustrated in FIG. 25, the control circuit 170 causes the display 200 to display content designated by a user, for example, on the basis of a user's instruction (Step S1). FIG. 26A schematically illustrates an example of the content displayed on the display 200. In this example, a novel is displayed by an electronic book app. The user can watch the content displayed on the display 200 through the light transmitting part 160. FIG. 26B schematically illustrates how the eye 500 looks in this state, and the size of a pupil is normal.

Figure 27A:
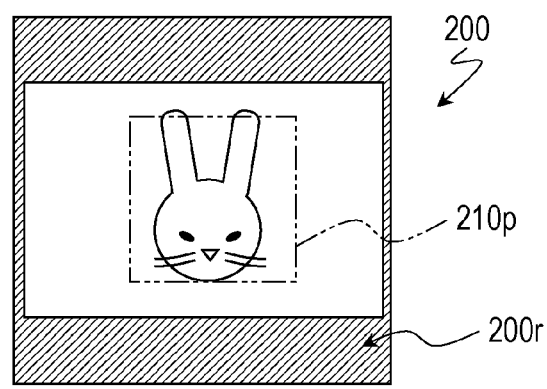
FIG. 27A is a view schematically illustrating a state where an image displayed on the display is switched to an image that interests a user.
Figure 27B:
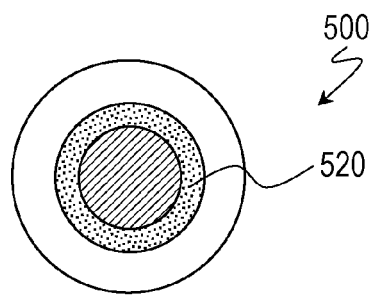
FIG. 27B is a view schematically illustrating how an eye looks when an image that interests a user is displayed on the display.

Next, the control circuit 170 switches the image displayed on the display 200 to an image that interests the user at a certain timing as schematically illustrated in FIG. 27A (Step S2). The image that interests the user can be any image (e.g., a user's favorite animal or food, something the user wants to buy, an image of a user's lover) that excites a user's sympathetic nerve. For example, during execution of a game app, such an image can be displayed naturally in the middle of the game. When the image that interests the user is displayed, the pupil becomes larger as schematically illustrated in FIG. 27B. As a result, light more easily reaches a fundus.

Next, the control circuit 170 drives the imaging device 130G to image the eye 500 (Step S3). Then, the control circuit 170 determines whether or not the pupil has become large enough on the basis of the obtained image (Step S4). For example, whether or not mydriasis is occurring can be determined by measuring a diameter of the pupil by image processing and comparing a value obtained by the measurement and a preset threshold value. The imaged used for the determining process may be an image obtained by the first camera unit or may be an image obtained by the second camera unit. Since light expressing the image that interests the user is used as lighting, image quality of the obtained image is sometimes low, but it is only necessary that the image quality is high enough to determine whether or not mydriasis is occurring.

In a case where the pupil has not become large, the processing returns to Step S2, where the image displayed on the display 200 is switched to another image that is considered to interests the user. Meanwhile, in a case where mydriasis is detected, the control circuit 170 causes the display 200 to display a lighting pattern for imaging a fundus and causes the first camera unit (the first camera units 131a through 131h in this case) of the imaging device 130G to image the eye 500 (Step S5).

Figure 28A:
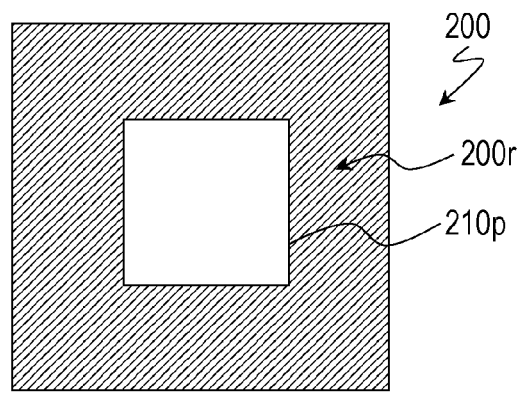
FIG. 28A is a plan view illustrating an example of a lighting pattern for imaging a fundus.

FIG. 28A illustrates an example of the lighting pattern for imaging a fundus. In this example, the polarizer 210p disposed in front of the display 200 has a rectangular shape, and the control circuit 170 causes a rectangular region of the display 200 that overlaps the polarizer 210p to selectively emit light. In this case, the half mirror 120 is irradiated with linearly-polarized light, and the linearly-polarized light reflected by the half mirror 120 enters the eye 500. That is, in the configuration illustrated in FIG. 24, the first region Q1 of the display 200 and the polarizer 210p constitute the first illuminating unit for offering illuminating light for imaging a fundus.

Figure 28B:
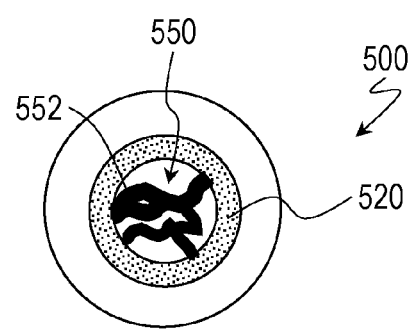
FIG. 28B is a view schematically illustrating an example of an image of an eye obtained in a state where the lighting pattern for imaging a fundus is displayed.

FIG. 28B schematically illustrates an example of an image of an eye obtained in the state where the lighting pattern for imaging a fundus is displayed. It is possible to obtain an image in which texture concerning a blood vessel 552 and the like on a retina clearly appears, as in the example illustrated in FIG. 4.

In this example, the control circuit 170 executes imaging of a cornea following imaging of a fundus. In order to image a cornea, the control circuit 170 terminates irradiation of the half mirror 120 with the lighting pattern for imaging a fundus by controlling driving of the display 200, causes the display 200 to display a lighting pattern for imaging a cornea, and causes the second camera unit 132 of the imaging device 130G to image the eye 500 (Step S6).

Figure 39:
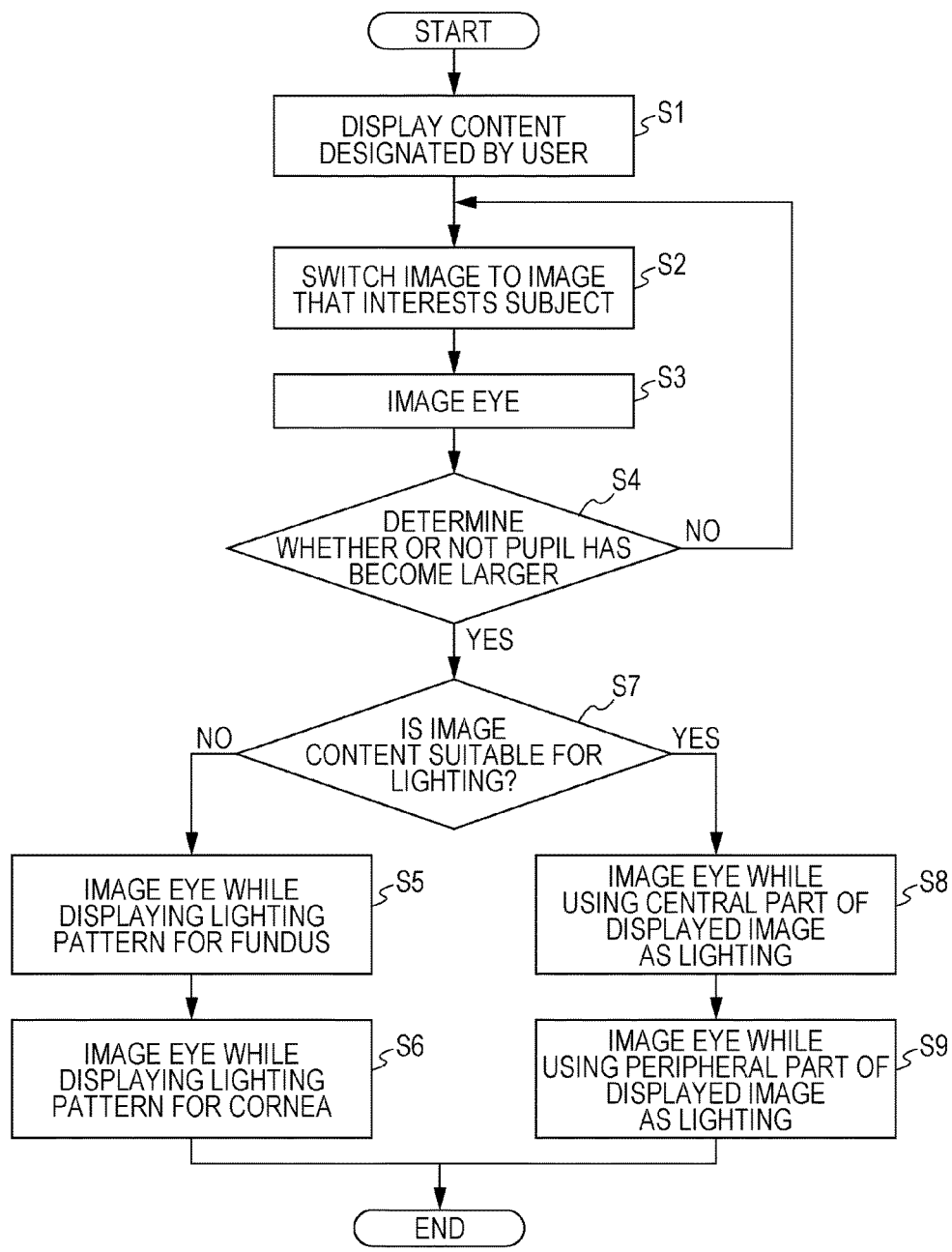
FIG. 39 is a flowchart for explaining an example of an eye imaging operation performed by the eye imaging apparatus.

FIG. 39 is another flowchart for explaining an example of an eye imaging operation performed by the eye imaging apparatus 100H. A difference from FIG. 25 is that in a case where a result of the process in Step S4 for determining whether or not the pupil has become large is YES, it is determined whether or not image content that is being displayed is appropriate for lighting (Step S7). Specifically, it is determined whether or not the displayed image is close to grey on the average instead of containing too much specific single-color. More specifically, a color balance of three kinds of values E(R), E(G), and E(B) obtained by adding and averaging RGB values that constitute a color image is evaluated, and in a case where E(R)/E(G)<TH1 and E(B)/E(G)<TH2 (TH1 and Th2 are constant values) are satisfied, a light distribution of image content is close to grey that is an achromatic color instead of containing too much specific color, and the displayed image can be used as it is as illuminating light for obtaining a fundus image. In this case, the fundus is imaged by using an image of the central part Q1 of the displayed image as polarized lighting (Step S8). In this case, luminance of an image in the peripheral part Q2 may be decreased. This has a secondary effect of further widening the pupil. Next, the cornea is imaged by using image content in the peripheral part Q2 of the displayed image (Step S9). In this case, the cornea is obliquely irradiated with unpolarized light by decreasing luminance of the image in the central part Q1.

Figure 29A:
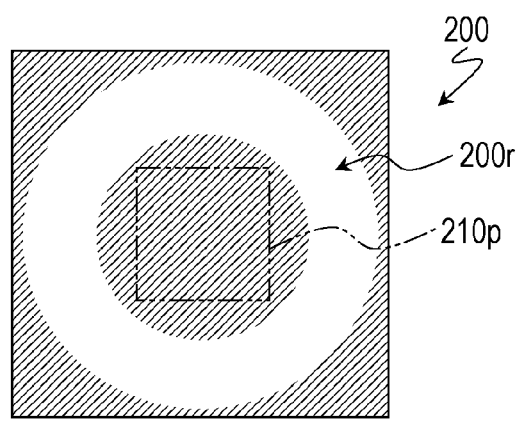
FIG. 29A is a plan view illustrating an example of a lighting pattern for imaging a cornea.

FIG. 29A illustrates an example of a lighting pattern for imaging a cornea. In this example, the control circuit 170 causes part of the second region Q2 that surrounds the first region Q1 of the display surface 200r to selectively emit light so that the part of the second region Q2 emits light in a ring shape. The control circuit 170 may cause the whole second region Q2 to emit light. The half mirror 120 can thus be irradiated with ring-shaped lighting as in the example described with reference to FIG. 5. That is, in the configuration illustrated in FIG. 24, at least part of the second region Q2 of the display 200 constitutes the second illuminating unit that offers illuminating light for imaging a cornea. In this example, since no polarizer is disposed above the second region Q2, the half mirror 120 is irradiated with unpolarized light. Although both of the broken-line arrow indicative of the reflected light R1 and the broken-line arrow indicative of the reflected light R2 are illustrated in FIG. 24, this intends to merely save a page and does not intend that the eye 500 is irradiated with the reflected light R1 and the reflected light R2 at the same timing.

Figure 29B:
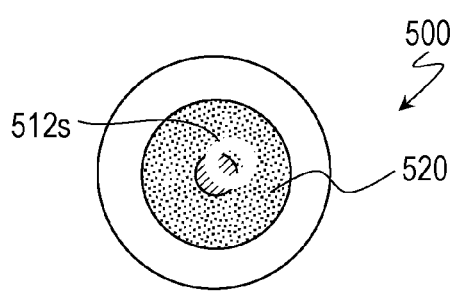
FIG. 29B is a view schematically illustrating an example of an image of an eye obtained in a state where the lighting pattern for imaging a cornea is displayed.

FIG. 28B schematically illustrates an example of an image of an eye obtained in a case where a lighting pattern for imaging a cornea is displayed. After imaging of the fundus, the pupil contracts again due to influence of surrounding lighting, but an image including an image of a bright spot generated by specular reflection on the surface of the cornea 510 and vicinity thereof can be obtained as in the example illustrated in FIG. 6 by irradiation at a larger incident angle with the reflected light R2 reflected by the half mirror 120. In the example illustrated in FIG. 29B, a ring-shaped bright part 512s generated by specular reflection on the surface of the cornea 510 and vicinity thereof appears in the image as in the example illustrated in FIG. 6.

As described above, according to Third Embodiment, sensing of an eye can be performed by the eye imaging apparatus 100H under a certain condition or at a certain timing while usually causing the eye imaging apparatus 100H to operate as a display device. For example, sensing of an eye can be executed without user's awareness by incorporating the eye imaging apparatus 100H into, for example, a general tablet terminal. In particular, sensing of an eye can be effectively executed without user's awareness by deciding what kind of image or video is to be presented to the user in consideration of user's preference. The eye imaging apparatus according to the present disclosure can be incorporated not only into a mobile device, but also into a mirror at home, for example. This leads to a possibility that monitoring of intraocular pressure of a patient with glaucoma, monitoring of a blood glucose concentration in aqueous humor of a patient with diabetes, monitoring of beta-amyloid in the retina of an elderly person for early detection of Alzheimer's Disease can be executed by imaging an eye on a daily basis in a non-invasive manner in a short period.

Fourth Embodiment

In the embodiments described above, a clearer image is obtained by blocking light in a specific polarization plane of return light from an eye by using the polarizer 140A especially in imaging of a fundus. However, information on a polarization state of return light may be used for observation of an eye by actively obtaining the information on the polarization state as described below.

Figure 30:
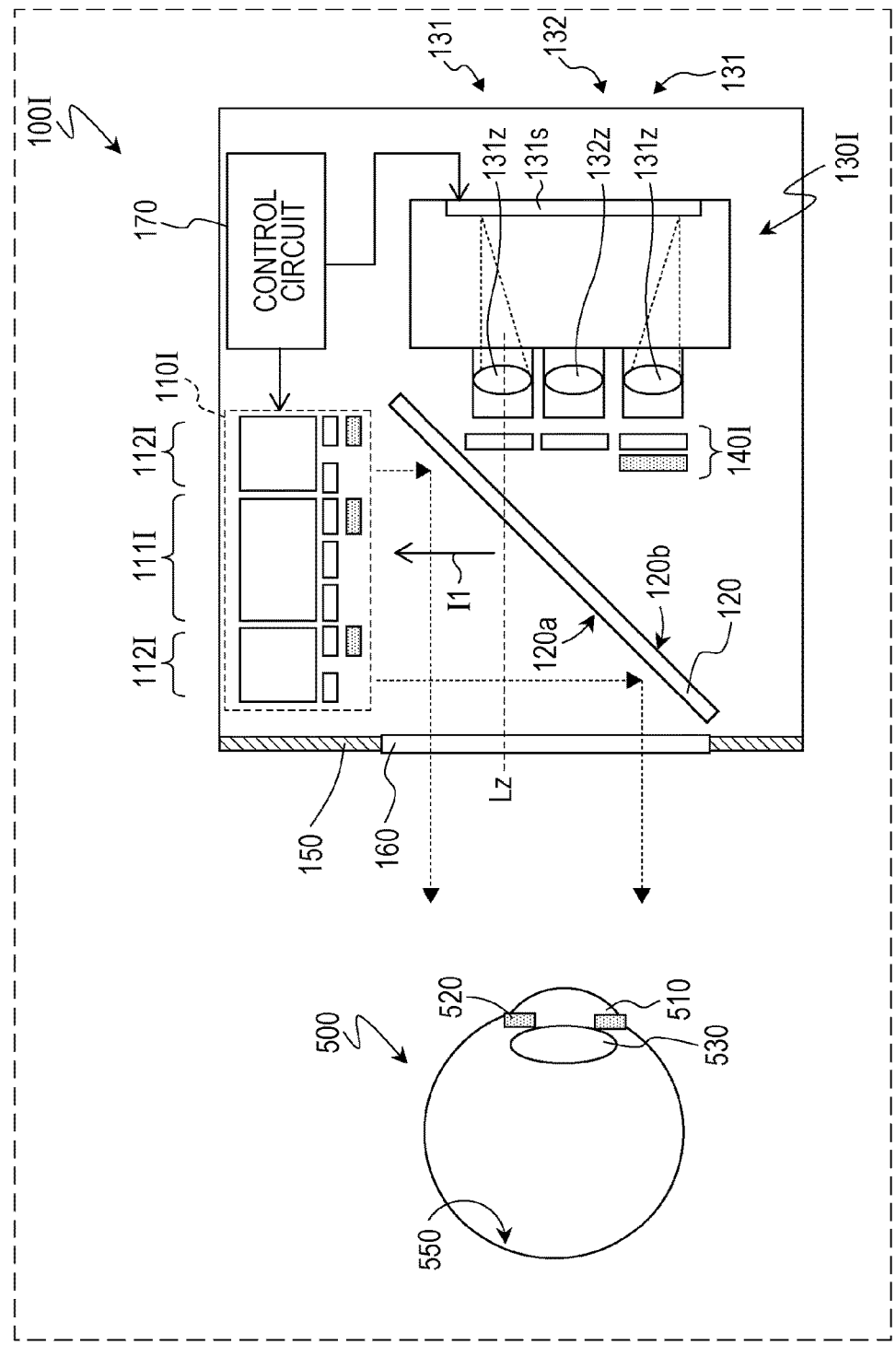
FIG. 30 is a view schematically illustrating an exemplary configuration of an eye imaging apparatus according to Fourth Embodiment of the present disclosure.

FIG. 30 schematically illustrates an exemplary configuration of an eye imaging apparatus according to Fourth Embodiment of the present disclosure. An eye imaging apparatus 100I illustrated in FIG. 30 includes a lighting device 110I including a first illuminating unit 111I and a second illuminating unit 112I and an imaging device 130I including a plurality of camera units 131. As in the example described with reference to FIG. 22, a plurality of objective lenses 131z in the imaging device 130I are arranged, for example, in a matrix of three rows and three columns when viewed along an optical axis Lz of the objective lenses 131z. Furthermore, the eye imaging apparatus 100I includes a polarizer 140I between a half mirror 120 and the plurality of camera units 131. The polarizer 140I includes a plurality of polarizing plates located in front of the respective camera units. At least one of the plurality of polarizing plates is a linearly polarizing plate, and a transmission axis thereof is parallel, for example, with a top-bottom direction of the paper on which FIG. 30 is drawn.

Figure 31:
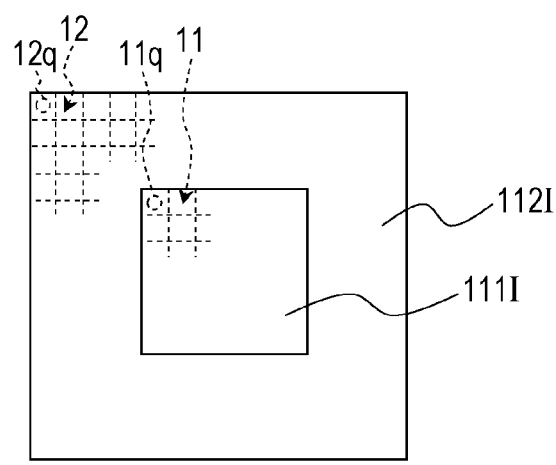
FIG. 31 is a plan view of a first illuminating unit and a second illuminating unit when viewed from a direction indicated by arrow I1 in FIG. 30.

FIG. 31 illustrates the first illuminating unit 111I and the second illuminating unit 112I viewed from the direction indicated by arrow I1 in FIG. 30. In the configuration illustrated in FIG. 31, the first illuminating unit 111I has a rectangular shape as a whole, and the second illuminating unit 112I is located outside the first illuminating unit 111I. In this example, an external shape of the second illuminating unit 112I is also rectangular.

As schematically illustrated in FIG. 31, the first illuminating unit 111I includes a plurality of light emitting units 11 each including a light source 11q such as an LED. The light source 11q is, for example, configured so that on an off can be controlled independently, and the first illuminating unit 111I is driven per light emitting unit 11. Similarly, in this example, the second illuminating unit 112I includes a plurality of light emitting units 12 each including a light source 12q. The second illuminating unit 112I is driven per light emitting unit 12 as in the case of the first illuminating unit 111I.

Figure 32:
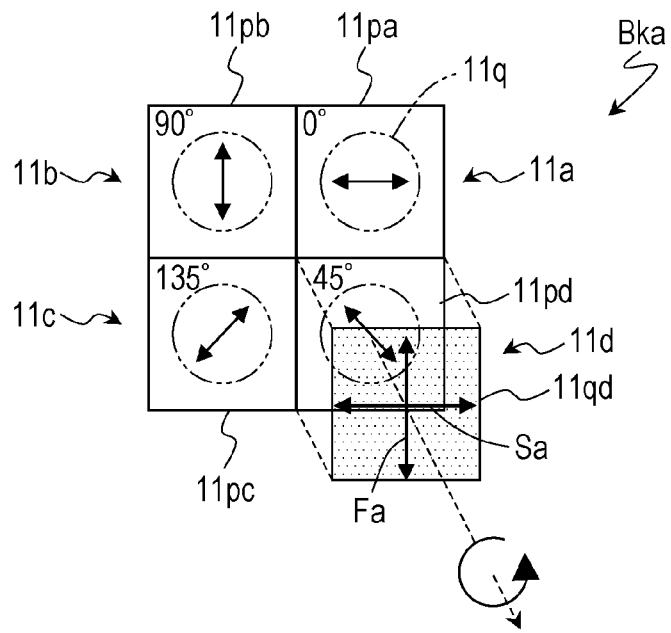
FIG. 32 is a view schematically illustrating four light emitting units among light emitting units of the first illuminating unit.

FIG. 32 schematically illustrates four light emitting units 11 among the light emitting units 11 of the first illuminating unit 111I. FIG. 32 illustrates four light emitting units 11a through 11d arranged in two rows and two columns. Linearly polarizing plates 11pa through 11pd having transmission axes in respective different directions are disposed in front of the respective light sources 11q of the light emitting units 11a through 11d. In the example illustrated in FIG. 32, directions of the transmission axes of the linearly polarizing plates 11pa through 11pd are 0 degree, 90 degrees, 135 degrees, and 45 degrees, respectively. One of the transmission axes of the linearly polarizing plates 11pa through 11pd is orthogonal to a transmission axis of one of the at least one linearly polarizing plate of the polarizer 140I.

In the example illustrated in FIG. 32, the light emitting unit 11d further includes a ¼ wave plate (λ/4 plate) 11qd disposed in front of the linearly polarizing plate 11pd. The ¼ wave plate 11qd is disposed above the linearly polarizing plate 11pd so that a fast axis Fa and a slow axis Sa thereof form an angle of 45 degrees with the transmission axis of the linearly polarizing plate 11pd. As schematically illustrated in FIG. 32, a laminated body made up of the linearly polarizing plate 11pd and the ¼ wave plate 11qd functions as a circularly polarizing plate.

The first illuminating unit 111I has a structure in which a light emitting block Bka including the light emitting units 11a through 11d is repeated. The half mirror 120 can be irradiated with linearly-polarized light having an electric field vector oscillating in a direction of 0 degree by selectively turning on the light sources 11q of the light emitting units 11a together. Linearly-polarized light having an electric field vector oscillating in a direction of 90 degrees is obtained in a case where the light sources 11q of the light emitting units 11b are selectively turned on together, and linearly-polarized light having an electric field vector oscillating in a direction of 135 degrees is obtained in a case where the light sources 11q of the light emitting units 11c are selectively turned on together. In a case where the light sources 11q of the light emitting units 11d are selectively turned on together, counterclockwise circularly-polarized light is emitted when viewed from a direction opposite to a travel direction of the light as schematically illustrated in FIG. 32. In this example, the first illuminating unit 111I is configured to be capable of generating four different types of polarized light including circularly-polarized light.

Figure 33:
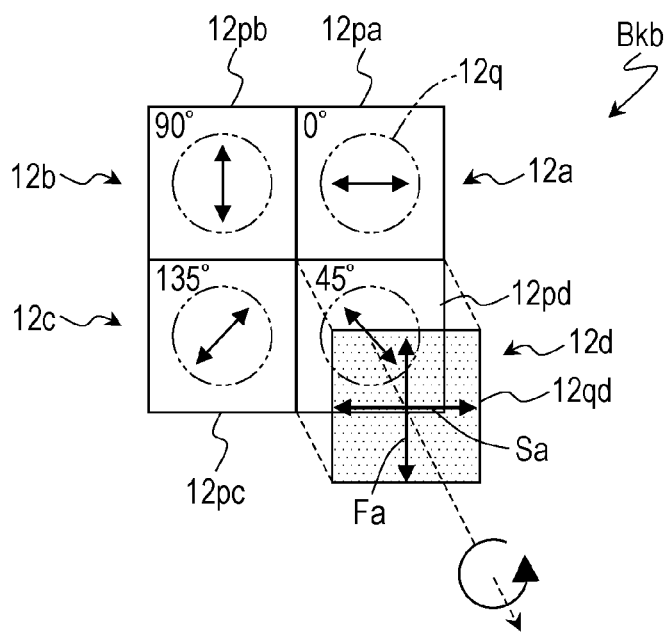
FIG. 33 is a view schematically illustrating four light emitting units among light emitting units of the second illuminating unit.

FIG. 33 schematically illustrates four light emitting units 12 among the light emitting units 12 of the second illuminating unit 112I. The second illuminating unit 112I is also configured to be capable of switching among a plurality of types of polarized light including linearly-polarized light and circularly-polarized light, as in the case of the first illuminating unit 111I. The light emitting units 12 of the second illuminating unit 112I includes light emitting units 12a through 12d. FIG. 33 illustrates a light emitting block Bkb including the four light emitting units 12a through 12d arranged in two rows and two columns among the plurality of light emitting units 12. The second illuminating unit 112I has a structure in which the light emitting block Bkb is repeated.

In the configuration illustrated in FIG. 33, the light emitting units 12a through 12d have linearly polarizing plates 12pa through 12pd disposed in front of respective light sources 12q, respectively. Directions of transmission axes of the linearly polarizing plates 12pa through 12pd are 0 degree, 90 degrees, 135 degrees, and 45 degrees, respectively. The light emitting unit 12d further includes a ¼ wave plate 12qd disposed in front of the linearly polarizing plate 12pd, and a laminated body made up of the linearly polarizing plate 12pd and the ¼ wave plate 12qd functions as a circularly polarizing plate.

In the configuration illustrated in FIGS. 32 and 33, the light emitting blocks Bka and Bkb each includes four light emitting units that emit light in different polarization states. Note, however, that the number of light emitting units included in each of the light emitting blocks Bka and Bkb is not limited to four. For example, the light emitting blocks Bka and/or Bkb may include sixteen light emitting units that emit light in different polarization states.

In this example, polarized light emitted from the first illuminating unit 111I is used to image a fundus 550, and polarized light emitted from the second illuminating unit 112I is used to image a cornea 510. The polarized light emitted from the first illuminating unit 111I is reflected toward an eye 500 by the half mirror 120. The polarized light emitted from the second illuminating unit 112I is also reflected toward the eye 500 by the half mirror 120. Use of an unpolarizing half mirror that reflects light without changing a polarization state as the half mirror 120 makes it possible to irradiate the eye 500 with one selected from a plurality of types of polarized light having different polarization directions and circularly-polarized light. Nerve fibers of the retina, the cornea 510, and the like of the eye 500 are transparent but have a birefringent property. Accordingly, return light from the fundus 550 and return light from the cornea 510 has a polarization state different from that before entry. The return light passes through the half mirror 120 and reaches the objective lens 131z of each camera unit 131.

Figure 34:
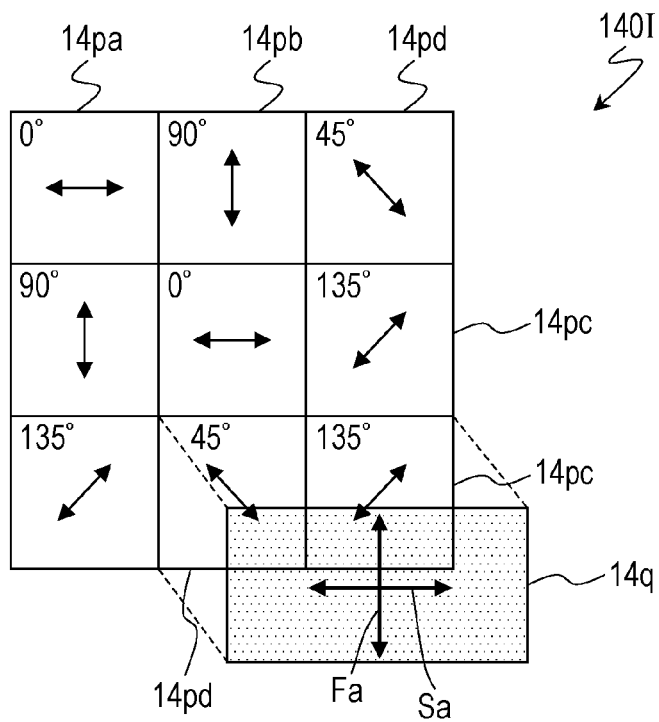
FIG. 34 is a plan view illustrating an exemplary configuration of a polarizer when viewed along an optical axis of an objective lens.

FIG. 34 illustrates an exemplary configuration of the polarizer 140I viewed along the optical axis Lz of the objective lens 131z. In the configuration illustrated in FIG. 34, the polarizer 140I has a plurality of linearly polarizing plates 14pa through 14pd arranged in a matrix of three rows and three columns corresponding to the objective lenses 131z of the camera units 131 arranged in a matrix. Any of the linearly polarizing plates 14pa through 14pd is located in front of each of the camera units 131.

Directions of the transmission axes of the linearly polarizing plates 14pa through 14pd are 0 degree, 90 degrees, 135 degrees, and 45 degrees, respectively. That is, at least one of the transmission axes of the linearly polarizing plates included in the polarizer 140I is orthogonal to one of the transmission axes of the linearly polarizing plates 11pa through 11pd included in the first illuminating unit 111I and one of the transmission axes of the linearly polarizing plates 12pa through 12pd included in the second illuminating unit 112I. Furthermore, at least one of the transmission axes of the linearly polarizing plates included in the polarizer 140I is parallel with one of the transmission axes of the linearly polarizing plates 11pa through 11pd included in the first illuminating unit 111I and one of the transmission axes of the linearly polarizing plates 12pa through 12pd included in the second illuminating unit 112I. Furthermore, a ¼ wave plate 14q is disposed above the linearly polarizing plate 14pd at a third row and a second column and the linearly polarizing plate 14pc at the third row and a third column. As illustrated in FIG. 34, a fast axis Fa and a slow axis Sa of the ¼ wave plate 14q are adjusted to directions of 90 degrees and 0 degree, respectively, and a laminated body made up of the linearly polarizing plate 12pc and the ¼ wave plate 14q and a laminated body made up of the linearly polarizing plate 12pd and the ¼ wave plate 14q function as circular polarizing plates.

As described above, the nerve fibers of the retina, the cornea 510, and the like of the eye 500 exhibit birefringence and change a polarization state of incident light. Stokes parameters concerning return light can be estimated on the basis of data obtained after parallax correction by imaging the eye 500 by using each of the plurality of camera units 131 in front of which a linearly polarizing plate or a circular polarizing plate is disposed and performing parallax correction on obtained image data. That is, a polarization state of return light can be found on the basis of data obtained after parallax correction.

Figure 35:
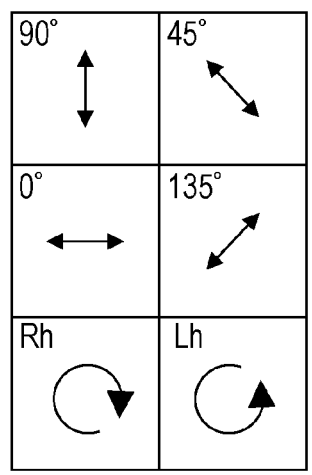
FIG. 35 is a view schematically illustrating polarization states of light entering six objective lenses located in a second column and a third column of a matrix of three rows and three columns illustrated in FIG. 34.

FIG. 35 schematically illustrates polarization states of light entering the six objective lenses 131z located at the second and third columns of the matrix of three rows and three columns illustrated in FIG. 34. Images obtained by six camera units 131 located at the second and third columns of the matrix of three rows and three columns are four images based on linearly-polarized light having polarization directions of 90 degrees, 45 degrees, 0 degree, and 135 degrees, and an image based on clockwise circularly-polarized light and an image based on counterclockwise circularly-polarized light. Since these six images are images obtained from different viewpoints, parallax exists among these images. Influence of the parallax among these six images can be cancelled, for example, by image processing of parallax correction. For example, a method described in Kuniyuki KUGENUMA "Parallax estimation and image synthesis from low-SNR multi-aperture images", 2016, Optics & Photonics Japan 2016, 31aES9, entire contents of which are hereby incorporated by reference, can be applied as parallax correction.

For example, the images obtained after parallax correction, i.e., the four images based on linearly-polarized light having polarization directions of 90 degrees, 45 degrees, 0 degree, and 135 degrees, and the image based on clockwise circularly-polarized light and the image based on counterclockwise circularly-polarized light are expressed as $I_{90}$, $I_{45}$, $I_0$, $I_{135}$, $I_{Rh}$, and $I_{Lh}$, respectively. In this case, images $I(S_0)$, $I(S_2)$, and $I(S_3)$ expressed by Stokes parameters concerning return light can be calculated by the following formula (1):

$$I(S_0) = I_0 + I_{90}$$

$$I(S_1) = I_0 - I_{90}$$

$$I(S_2) = I_{45} - I_{135}$$

$$I(S_3) = I_{Rh} - I_{Lh} \tag{1}$$

Figure 36:
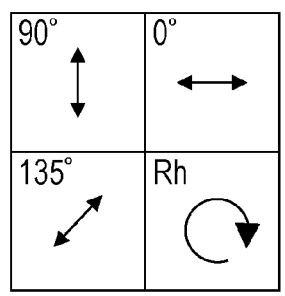
FIG. 36 is a view schematically illustrating polarization states of light entering four objective lenses located in a second row and first and second columns and a third row and first and second columns of the matrix of three rows and three columns illustrated in FIG. 34.

It is also possible to calculate $I(S_0)$ through $I(S_3)$ from a combination of objective lenses located in a block of two rows and two columns for which parallax between images is considered to be smaller. FIG. 36 schematically illustrates polarization states of light entering four objective lenses 131z located in the second row and the first and second columns and third row and the first and second columns of the matrix of three rows and three columns illustrated in FIG. 34. When images expressed as $I_{90}$, $I_0$, $I_{135}$, and $I_{Rh}$ are extracted, $I(S_0)$ through $I(S_3)$ can be calculated on the basis of the following formula (2) where "*" indicates multiplication:

$$I(S_0) = I_0 + I_{90}$$

$$I(S_1) = I_0 - I_{90}$$

$$I(S_2) = (I_0 + I_{90}) - 2 * I_{135}$$

$$I(S_3) = 2 * I_{Rh} - (I_0 + I_{90}) \tag{2}$$

For example, the eye 500 can be irradiated with circularly-polarized light in a state close to coaxial lighting by causing the light sources 11q of the light emitting units 11d to selectively turn on among the plurality of light emitting units 11 of the first illuminating unit 111I (see FIG. 32). By obtaining an image based on return light from the eye 500 irradiated with the circularly-polarized light by using the imaging device 130I, information concerning birefringence of transparent cornea and retina of a fundus that can be regarded as optical media can be obtained from the obtained image. According to Non-Patent Literature 1, the thickness of optic nerve fibers of retina that is useful for diagnosis of glaucoma, which produces no symptoms and is therefore hard to detect early, can be estimated from return light from an eye irradiated with circularly-polarized light. That is, according to Fourth Embodiment, diagnosis of glaucoma and monitoring of a patient suspected of having glaucoma are possible through imaging of an eye.

According to the configuration described with reference to FIGS. 30 through 36, the eye 500 can be irradiated while switching among four types of polarized light. Furthermore, stokes parameters $S_{00}$, $S_{01}$, $S_{02}$, and $S_{03}$ concerning light with which the eye 500 is irradiated are known. It is therefore possible to find matrix elements of a Mueller matrix concerning the eye 500 by irradiating the eye 500 while switching among four types of polarized light and obtaining and analyzing data of images $I(S_0)$, $I(S_1)$, $I(S_2)$, and $I(S_3)$ concerning return light for each irradiation with light having different polarization states. As a result, more detailed optical information concerning the cornea 510 and retina nerve fibers of the eye 500 can be obtained from the matrix elements of the Mueller matrix.

Figure 37:
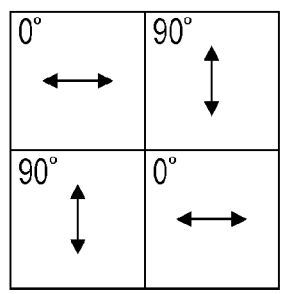
FIG. 37 is a view schematically illustrating polarization states of light entering four objective lenses located in a first row and first and second columns and a second row and first and second columns of the matrix of three rows and three columns illustrated in FIG. 34.

FIG. 37 schematically illustrates polarization states of light entering four objective lenses 131z located in the first row and the first and second columns and the second row and the first and second columns of the matrix of three rows and three columns illustrated in FIG. 34. In the example illustrated in FIG. 37, a polarization plane of linearly-polarized light that enters the objective lens 131z in one of two camera units 131 adjacent in a row direction or a column direction is orthogonal to a polarization plane of linearly-polarized light that enters the objective lens 131z in the other one of the two camera units 131. It is therefore possible to obtain a parallel-nicols image and a crossed-nicols image concerning the cornea 510, for example, by imaging the cornea 510 by causing the second illuminating unit 112I to emit linearly-polarized light having a polarization direction of 0 degree and imaging the cornea 510 by causing the second illuminating unit 112I to emit linearly-polarized light having a polarization direction of 90 degrees. If a parallel-nicols image and a crossed-nicols image concerning the cornea 510 can be obtained, a scratch and the like on the cornea 510 can be clearly observed and a cross pattern caused by birefringence can be observed as described in Non-Patent Literature 2 on the basis of these images.

In Fourth Embodiment, a lighting device is configured to be capable of irradiating an eye while switching among plural types of polarized light, and plural types of polarizing plates are disposed in front of a plurality of respective camera units. Therefore, a polarization state of return light can be analyzed in more detail on the basis of obtained images. It is therefore possible to obtain information concerning an optical property of a transparent medium that is hard to obtain just by general image processing.

The embodiments of the present disclosure are useful for imaging of an eye. According to the embodiments of the present disclosure, images useful for inspection of an eye such as an image of a fundus and an image of a cornea can be obtained in a relatively short time without restraining a subject. Furthermore, it is unnecessary to use different apparatuses for imaging of a fundus and imaging of a cornea, and it is therefore possible to inspect the whole eye at one time. The embodiments of the present disclosure are advantageous especially for inspection of an eye of a subject, such as an animal or an infant, who cannot understand a doctor's instruction. The embodiments of the present disclosure make it possible to image an eye without subject's awareness and are therefore suitable for daily monitoring of health.

What is claimed is:

1. An eye imaging apparatus comprising:
    a lighting device;
    a half mirror;
    an imaging device; and
    a first polarizer,
    wherein the lighting device includes a fundus illuminator and a cornea illuminator,
    wherein the imaging device includes a first camera having a first objective lens,
    wherein the first polarizer is disposed between the half mirror and the first camera,
    wherein the fundus illuminator irradiates the half mirror with first light polarized in a direction orthogonal to a transmission axis of the first polarizer,
    wherein the half mirror receives the first light and outputs resulting light to an eye, a travel direction of the resulting light being in alignment with an optical axis of the first objective lens,
    wherein the cornea illuminator emits light at a timing different from a timing at which the fundus illuminator emits the first light, and
    wherein second light based on the light emitted by the cornea illuminator irradiates the eye from a direction different from a direction parallel with the optical axis of the first objective lens.

2. The eye imaging apparatus according to claim 1,
    wherein the cornea illuminator is disposed to surround the fundus illuminator and includes a plurality of light emitters that emit the light,
    wherein the half mirror is irradiated with the light that is unpolarized light, and
    wherein the second light is light reflected by the half mirror.

3. The eye imaging apparatus according to claim 1,
    wherein the cornea illuminator is disposed to surround the first objective lens when viewed along the optical axis and includes a plurality of light emitters that emit the light,
    wherein the half mirror is irradiated with the light that is unpolarized light, and
    wherein the second light is light that has passed through the half mirror.

4. The eye imaging apparatus according to claim 1,
    wherein the cornea illuminator includes a plurality of light emitters that emit the light,
    wherein the cornea illuminator is disposed on a side of the half mirror opposite to a side on which the first camera is disposed, and
    wherein the plurality of light emitters are disposed not to overlap the optical axis and not to overlap a straight line that is parallel with the optical axis and that intersects with the first objective lens.

5. The eye imaging apparatus according to claim 2,
    wherein the plurality of light emitters include a plurality of first light sources and a plurality of second light sources,
    wherein the cornea illuminator includes first linearly polarizing plates disposed in front of the respective first light sources,
    wherein transmission axes of the respective first linearly polarizing plates are orthogonal to the transmission axis of the first polarizer, and
    wherein the plurality of first light sources emit light at a timing different from a timing at which the plurality of second light sources emit light.

6. The eye imaging apparatus according to claim 1,
    wherein the imaging device further includes a second camera having a second objective lens, and
    wherein the first polarizer is disposed between the half mirror and the second camera.

7. The eye imaging apparatus according to claim 6,
    wherein a focal length of the second objective lens is shorter than a focal length of the first objective lens.

8. The eye imaging apparatus according to claim 6,
    wherein the imaging device includes a plurality of first cameras,
    wherein the plurality of first cameras include the first cameras,
    wherein the plurality of first cameras include a plurality of first objective lenses,
    wherein the plurality of first objective lenses include the first objective lenses,
    wherein the plurality of first cameras correspond to the respective plurality of first objective lenses, and
    wherein the plurality of first objective lenses surround the second objective lens when viewed along the optical axis.

9. The eye imaging apparatus according to claim 8,
    wherein a focal length of the second objective lens is shorter than a focal length of each of the plurality of first objective lenses.

10. The eye imaging apparatus according to claim 1,
    wherein the lighting device is a display having a display surface,
    wherein the fundus illuminator includes a first region of the display surface and a second polarizer disposed in front of the first region,
    wherein a transmission axis of the second polarizer is orthogonal to the transmission axis of the first polarizer, and wherein the cornea illuminator includes a second region of the display surface, the second region surrounding the first region.

11. The eye imaging apparatus according to claim 10, further comprising a control circuit that drives the lighting device and the imaging device in synchronization with each other,
wherein the display switches a displayed image among a plurality of images, and
wherein the control circuit causes the imaging device to detect mydriasis of the eye, and upon detection of mydriasis, the control circuit causes the fundus illuminator to emit the first light and causes the imaging device to image the eye.

12. The eye imaging apparatus according to claim 11,
wherein, following the imaging under the first light, the control circuit causes the fundus illuminator to finish the irradiation with the first light, and causes the imaging device to image the eye while causing the cornea illuminator to emit light.

13. The eye imaging apparatus according to claim 1,
wherein one of the fundus illuminator and the cornea illuminator includes a first light emitter including a first linearly polarizing plate, a second light emitter including a second linearly polarizing plate, a third light emitter including a third linearly polarizing plate, and a fourth light emitter including a first circularly polarizing plate,
wherein directions of transmission axes of the first, second, and third linearly polarizing plates are different from one another, and one of the transmission axes of the first, second, and third linearly polarizing plates is parallel with a polarization direction of the first light,
wherein the imaging device includes a plurality of first cameras each including the first camera,
wherein the first polarizer includes a fourth linearly polarizing plate having a transmission axis parallel with the polarization direction of the first light, a fifth linearly polarizing plate having a transmission axis orthogonal to the polarization direction of the first light, a sixth linearly polarizing plate having a transmission axis in a direction different from both of the transmission axis of the fourth linearly polarizing plate and the transmission axis of the fifth linearly polarizing plate, and a second circularly polarizing plate, and
wherein each of the fourth linearly polarizing plate, the fifth linearly polarizing plate, the sixth linearly polarizing plate, and the second circularly polarizing plate is disposed in front of one of the plurality of first cameras.

14. The eye imaging apparatus according to claim 13,
wherein the other one of the fundus illuminator and the cornea illuminator includes a fifth light emitter including a seventh linearly polarizing plate, a sixth light emitter including an eighth linearly polarizing plate, a seventh light emitter including a ninth linearly polarizing plate, and an eighth light emitter including a third circularly polarizing plate, and
wherein directions of transmission axes of the seventh, eighth, and ninth linearly polarizing plates are different from one another, and one of the transmission axes of the seventh, eighth, and ninth linearly polarizing plates is parallel with the polarization direction of the first light.

15. The eye imaging apparatus according to claim 1,
wherein the imaging device is a light field camera.

16. The eye imaging apparatus according to claim 1,
wherein the imaging device images a fundus of the eye while the eye is being irradiated with the reflected first light and images a cornea of the eye while the eye is being irradiated with the second light.

* * * * *